United States Patent [19]

Heindl et al.

[11] Patent Number: 5,624,943
[45] Date of Patent: Apr. 29, 1997

[54] PYRIDINE COMPOUNDS WHICH ARE USEFUL AS LEUKOTRIENE-$B_4$-ANTAGONISTS

[75] Inventors: Josef Heindl; Werner Skuballa; Bernd Buchmann; Wolfgang Fröhlich; Roland Ekerdt; Claudia Giesen, all of Berlin, Germany

[73] Assignee: Schering Aktiengesellschaft, Berlin, Germany

[21] Appl. No.: 374,608

[22] PCT Filed: Jul. 1, 1993

[86] PCT No.: PCT/DE93/00593

§ 371 Date: Apr. 27, 1995

§ 102(e) Date: Apr. 27, 1995

[87] PCT Pub. No.: WO94/02464

PCT Pub. Date: Feb. 3, 1994

[30] Foreign Application Priority Data

Jul. 21, 1992 [DE] Germany ............. 42 24 402.1

[51] Int. Cl.[6] .............. C07D 213/65; A61K 31/44
[52] U.S. Cl. .............. 514/345; 514/357; 514/354; 514/355; 514/277; 546/301; 546/314; 546/315; 546/334; 546/340; 546/341; 546/342
[58] Field of Search .............. 546/301, 314, 546/315, 334, 340, 341, 342; 574/345, 357, 354, 355, 277

[56] References Cited

FOREIGN PATENT DOCUMENTS

| | | | |
|---|---|---|---|
| 0303465 | 2/1989 | European Pat. Off. | 546/301 |
| 0402116 | 1/1991 | European Pat. Off. | 564/20 |
| 9118601 | 12/1991 | WIPO | 546/301 |
| 9118879 | 12/1991 | WIPO | 546/301 |

*Primary Examiner*—Zinna Northington Davis
*Attorney, Agent, or Firm*—Millen, White, Zelane, & Branigan, P.C.

[57] ABSTRACT

The invention relates to new pyridine derivatives of general formula I which have useful properties, e.g., as leukotriene-$B_4$-antagonists. Pharmaceutical compositions containing these compounds can be used to treat various diseases.

20 Claims, No Drawings

PYRIDINE COMPOUNDS WHICH ARE USEFUL AS LEUKOTRIENE-B₄-ANTAGONISTS

This application is a 371 of PCT/DE93/00593 filed Jul. 1, 1993.

The invention relates to new pyridine derivatives with leukotriene-B$_4$ antagonistic effect, a process for their production and their use as pharmaceutical agents.

Leukotriene-B$_4$ (LTB$_4$)

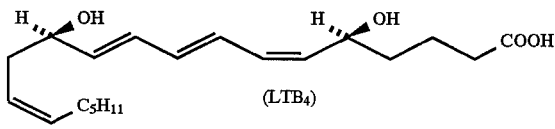

was discovered by B. Samuelsson et al. as a metabolite of the arachidonic acid.

The nomenclature of the leukotrienes can be found in the following works:
a) B. Samuelsson et al., Prostaglandins 19, 645 (1980); 17, 785 (1979).
b) C. N. Serhan et al., Prostaglandins 34, 201 (1987).

The physiological and especially the pathophysiological importance of leukotriene-B$_4$ is summarized in some more recent works:
a) The Leukotrienes, Chemistry and Biology eds. L. W. Chakrin, D. M. Bailey, Academic Press 1984. b) J. W. Gillard et alo, Drugs of the Future 12, 453 (1987). c) B. Samuelsson et al., Science 237, 1171 (1987). d) C. W. Parker, Drug Development Research 10, 277 (1987). It follows from the above that LTB$_4$ is an important inflammation mediator for inflammatory diseases, in which leukocytes invade the diseased tissue. The effects of LTB$_4$ are triggered on the cellular plane by the bond of LTB$_4$ on a specific receptor.

It is known concerning LTB$_4$ that it causes the adhesion of leukocytes on the blood vessel wall. LTB$_4$ is chemotactically effective, i.e., it triggers a directed migration of leukocytes in the direction of a gradient of increasing concentration. Furthermore, it indirectly changes the vascular permeability based on its chemotactic activity, and a synergism with prostaglandin E$_2$ is observed. LTB$_4$ obviously plays a decisive role in inflammatory, allergic and immunological processes.

Leukotrienes and especially LTB$_4$ are involved in skin diseases, which are accompanied by inflammatory processes (increased vascular permeability and formation of edemas, cellular infiltration), increased proliferation of the skin cells and itching, such as, for example, in eczemas, erythemas, psoriasis, pruritus and acne. Pathologically increased leukotriene concentrations are either causally involved in the development of many dermatitides, or there is a connection between the persistence of the dermatitides and the leukotrienes. Clearly increased leukotriene concentrations were measured, for example, in the skin of patients with psoriasis or atopic dermatitis.

Leukotrienes and especially LTB$_4$ are also involved in diseases of the internal organs, for which an acute or chronic inflammatory component was described; e.g., joint diseases (arthritis); diseases of the respiratory system (asthma, rhinitis and allergies); inflammatory intestinal diseases (colitis); as well as reperfusion damages (to the heart, intestinal or renal tissue), which result by the temporary pathological obstruction of blood vessels.

Further, leukotrienes and especially LTB$_4$ are involved in the disease of multiple sclerosis and in the clinical picture of shock (triggered by infections, burns or in complications in kidney dialysis or other extracorporeal perfusion techniques).

Leukotrienes and especially LTB$_4$ further have an effect on the formation of white blood cells in the bone marrow, on the growth of unstriped muscle cells, of keratinocytes and of B-lymphocytes. LTB$_4$ is therefore involved in diseases with inflammatory processes and in diseases with pathologically increased formation and growth of cells.

For example, leukemia or arteriosclerosis represent diseases with this clinical picture. By the antagonizing of the effects, especially by LTB$_4$, the active ingredients according to the invention and their forms of administration are specific medicines for diseases of humans and animals, in which especially leukotrienes play a pathological role.

The new pyridine derivatives with leukotriene-B$_4$-antagonistic effect are characterized by general formula I

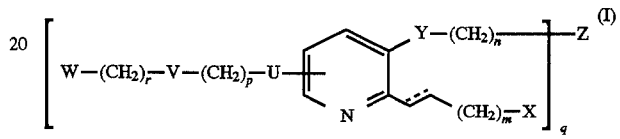

in which

........ symbolizes a single bond or a double bond, m, n, p and r each mean a number from 0 to 5, q represents the numbers 1 or 2, U symbolizes a single bond or the grouping —CH$_2$—CH$_2$—, —CHOH—, —CO—, —CH=CH—, —C≡C—, —CO—CO— or —CHOH—CHOH—, V means a single bond, a phenyl radical or a pyridyl radical, W means a hydrogen atom, a halogen atom, an alkyl group with up to 4 carbon atoms, a trifluoromethyl group, an alkylsulfonylamino group, a trifluoromethylsulfonylamino group, an arylsulfonylaminocarbonyl group, a free, esterified or amidated carboxyl group, or a hydroxy group, X symbolizes a free, esterified or amidated carboxyl group, Y represents an oxygen atom or a methylene group and Z is a single bond if q means the number 2 or otherwise means an alkyl group or alkylene group with at most 8 carbon atoms or a phenyl radical, phenoxy radical or styryl radical optionally substituted by alkyl groups with at most 4 carbon atoms, alkoxy groups with at most 4 carbon atoms, 1-oxoalkyl groups with at most 4 carbon atoms, halogen atoms and/or trifluoromethyl groups, and their salts with physiologically harmless bases.

As esterified or amidated carboxyl groups of the pyridine derivatives of general formula I, those are preferably considered that are derived from physiologically harmless alcohols or amines. Physiologically harmless alcohols, with which the carboxyl groups can be esterified, are, for example, straight-chain or branched, or cyclic, saturated or unsaturated hydrocarbon radicals, which optionally can be interrupted by an oxygen atom or a nitrogen atom, or can be substituted with hydroxy groups, amino groups or carboxyl groups, such as, for example, alkanols (especially those with 1 to 6 carbon atoms), alkenols, alkinols, cycloalkanols, cycloalkyl-alkanols, phenylalkanols, phenylalkenols, alkanediols, hydroxycarboxylic acids, aminoalkenols or alkylaminoalkenols and dialkylaminoalkanols with 1 to 4 carbon atoms in the alkyl radical.

Alcohols, which are suitable to esterify the carboxyl groups, are, for example, those that have a methylcarboxymethyl, ethyl-2-hydroxyethyl, 2-methoxyethyl, 2-aminoethyl, 2-dimethylaminoethyl, 2-carboxylethyl, propyl, allyl, cyclopropylmethyl, isopropyl, 3-hydroxypropyl, propinyl, 3-aminopropyl, butyl, sec-butyl, tert-butyl, butyl-(2), cyclobutyl, pentyl, isopentyl, tert-pentyl, 2-methylbutyl, cyclopentyl, hexyl, cyclohexyl, cyclo-2-enyl, cyclopentylmethyl, heptyl, benzyl, 2-phenylethyl, octyl, bornyl, isobornyl, menthyl, nonyl, decyl, 3-phenyl-propyl, 3-phenyl-prop-2-enyl, undecyl, or dodecyl radical. As alcohols suitable for esterification, those are also considered that result in labile esters, i.e., esters that can be cleaved under physiological conditions, such as 5-hydroxyindane, acyloxymethanols, especially acetoxymethanol, pivaloyloxymethanol, 5-indanyloxycarbonylmethanol, glycolic acid, dialkylaminoalkanols, especially dimethylaminopropanol, as well as hydroxyphthalide.

As physiologically harmless amines, with which the carboxyt groups can be amidated, preferably ammonia, alkylamines, dialkylamines, alkanolamines, dialkanolamines with 1 to 6 carbon atoms in the alkyl or alkanol radical or five-or six-membered N-heterocycles are preferably considered. As suitable amines, there can be mentioned, for example: the methylamine, the ethylamine, the isopropylamine, the ethanamine, the dimethylamine, the diethylamine, the diethanolamine, the pyrrolidine, the piperidine, the morpholine or the N-methyl-piperazine.

An alkylsulfonylamino group W preferably is to be understood to be a group that is derived from an alkyl group with at most 4 carbon atoms. For example, the methylsulfonylamino group can be mentioned.

An arylsulfonylaminocarbonyl group is to be understood to be, for example, an alkylbenzenesulfonylaminocarbonyl group with up to 4 carbon atoms in the alkyl radical—such as, for example, the 4-methylbenzenesulfonylaminocarbonyl group.

As physiologically compatible salts of the carboxyl group, there can be mentioned, for example, the alkali or alkaline-earth metal salts, such as the lithium salt, sodium salt, potassium salt or the calcium salt, the ammonium salt, the trishydroxymethylaminomethane salt and the copper(II) salt, salts with organic bases, such as the piperazine salt or the methylglucamine salt, as well as the salts of the pyridine derivatives with amino acids.

Within the scope of this invention, the following pyridine derivatives are especially preferred:

a) Pyridine derivatives of general formula I with X in the above-mentioned meaning with ..... meaning a single bond and among the latter again those with m meaning the number 0, b) Pyridine derivatives of general formula I with Y meaning an oxygen atom, n meaning a number from 1 to 4, q meaning the number 1 and Z meaning an alkyl group or alkenyl group with at most 8 carbon atoms and among the latter again those in which X, ..... and m have the meaning mentioned under a), c) Pyridine derivatives of general formula I with Y meaning an oxygen atom, n meaning a number from 1 to 4, q meaning the number 1 and Z meaning a phenyl radical, phenoxy radical or styryl radical, optionally substituted by alkyl groups with at most 4 carbon atoms, alkoxy groups with at most 4 carbon atoms and/or 1-oxoalkyl groups with at most 4 carbon atoms, and among the latter again those in which X, ..... and m have the meaning mentioned under a), d) Pyridine derivatives of general formula I with Y meaning an oxygen atom, n meaning a number from 1 to 5 and q meaning the number 2 and among the latter especially those in which X, ..... and m have the meaning mentioned under a), e) Pyridine derivatives of general formula I with p meaning the number 0, U and V meaning a single bond and W meaning a hydrogen atom or a halogen atom (especially a bromine atom or iodine atom) and among the latter again those in which X, Y, z, r, q, ..... n and m have the meaning mentioned under b), c) or d), and f) Pyridine derivatives of general formula I with p, U and V in the above-mentioned meaning and W meaning a hydrogen atom or a free, esterified or amidated carboxyl group and among the latter especially those in which X, Y, r, q, ..... n and m have the meaning mentioned under b), c) or d).

The invention further relates to a process for the production of the pyridine derivatives of general formula I, which is characterized in that in a way known in the art a) for the production of pyridine derivatives of general formula I with Y meaning an oxygen atom, a compound of general formula II

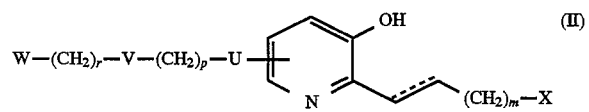

in which m, p, r, U, V, W and X have the above-mentioned meaning, is condensed in the presence of bases with a compound of general formula III or IV

in which n has the above-mentioned meaning,

Z' means the same as Z, but does not represent any single bond, and

Q represents a halogen atom, an alkylsulfonyloxy group or an arylsulfonyloxy group, or b) for the production of pyridine derivatives of general formula I with U meaning a grouping —CO—, —CH=CH—, —C≡C—, —CO—CO— or —CHOH—CHOH—, a compound of general formula V

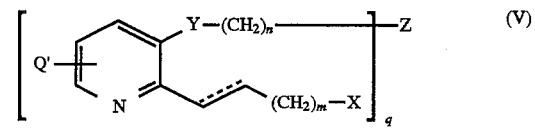

in which

....., m, n, p, q, X, Y and Z have the above-mentioned meaning and Q' means a halogen atom or a trifluoromethanesulfonyloxy group, is reacted with a compound of formula VI, VII or VIII

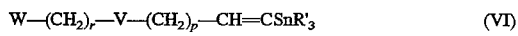

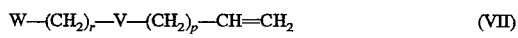

in which p, r, V and W have the above-mentioned meaning, and R' represent lower alkyl radicals with at most 4 carbon atoms, or c) for the production of pyridine derivatives of general formula I with U meaning the grouping —CH=CH—, a compound of general formula IX

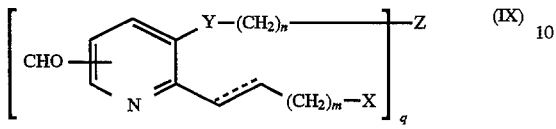

in which

....., m, n, q, X, Y and Z have the above-mentioned meaning, is condensed with a compound of general formula X

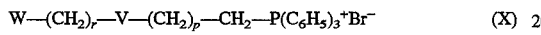

in which p, r, V and W have the above-mentioned meaning and optionally an existing triple bond is oxidized, existing oxo groups are reduced, existing multiple bonds are hydrogenated, existing hydroxy groups are alkylated, existing ester groups are saponified and/or existing carboxyl groups are esterified or converted to their amides or salts.

The process according to variant a) according to the invention is performed under the conditions that are used in a conventional way to alkylate aromatic or heteroaromatic hydroxy compounds. Thus, for example, the compounds of formula II can be alkylated in an inert solvent in the presence of alkali metal carbonates, such as potassium carbonate or cesium carbonate (J. Chem. Soc., Chem. Comm. 1979, 285) with the compounds of general formula III or IV, and in the latter case, pyridine derivatives of general formula I with q meaning number 2 are obtained. Also, the synthesis according to process variant b) takes place in a way known in the art, for example, by the compounds of formula V being reacted in the presence of organic palladium catalysts with the compounds of formula VI, VII or VIII (Tetrahedron Letters 50, 1975, 4467 ff, Bull. Chem. Soc. Jpn. 60, 1987, 767 ff; Angewandte Chemie [Applied Chemistry] 99, 1987, 1285 ff, Tetrahedron Letters 26, 1985, 2667 ff).

The process according to variant c) is performed under the conditions that are used in the usual way in the so-called Wittig reactions (Chem. Ber. 94, 1961, 1373 f).

The oxidation of the compounds of general formula I with U meaning a —C≡C— grouping to compounds with U meaning a —CO—CO— grouping takes place according to the method of Seebach (Helv. Chim. Acta. 71, 1988, 237 ff).

The conditions, under which the optionally following subsequent reactions are performed, are so conventional that no more detailed explanation is required.

The initial compounds required for the process according to the invention can also be synthesized in a way known in the art, for example, by the desired side chains, starting from the correspondingly substituted halopyridines, pyridine aldehydes or hydroxy pyridines esterified with trifluoromethanesulfonic acid, being synthesized under the above-mentioned conditions.

Thus, for example, the pyridine derivatives of general formula II with U meaning a —C≡C— or —CH$_2$—CH$_2$ group can be produced, by a compound of general formula XI

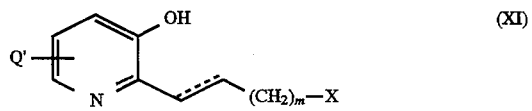

in which

....., m, X and Q' have the above-mentioned meaning, being reacted with a compound of general formula XII

in which p, r, V and W have the above-mentioned meaning and optionally the triple bond being hydrogenated.

The new pyridine derivatives are pharmacologically effective compounds, which are distinguished especially by a leukotriene-B$_4$ antagonistic effectiveness.

The pyridine derivatives of general formula I consequently have an anti-inflammatory, anti-allergic and anti-proliferative effect.

The compounds of formula I are especially suitable for topical administration, since they exhibit a dissociation between desired topical effectiveness and undesirable systemic side effects.

The new pyridine derivatives of formula I are suitable in combination with the additives and vehicles, usual in galenical pharmacy, for local treatment of diseases of the skin, in which leukotrienes play an important role, such as, for example, contact dermatitis, eczemas of the most varied type, neurodermatoses, erythrodermia, pruritis vulvae et ani, rosacea, lupus erythematosus cutaneous, psoriasis, lichen rubber planus et verrucosus and similar skin diseases.

The production of the pharmaceutical agent specialties takes place in the usual way, by the active ingredients being converted with suitable additives to the desired form of administration, such as, for example: solutions, lotions, ointments, creams or plasters.

In the thus formulated pharmaceutical agents, the active ingredient concentration is dependent on the form of administration. In the case of lotions and ointments, an active ingredient concentration of 0.0001% to 3% is preferably used.

Moreover, the new compounds optionally in combination with the usual vehicles and additives are also well-suited to produce inhalants, which can be used for the treatment of allergic diseases of the respiratory system, such as, for example, of bronchial asthma or rhinitis.

Further, the new pyridine derivatives are also suitable in the form of capsules, tablets or coated tablets, which preferably contain 0.1 to 100 mg of active ingredients or are administered orally or in the form of suspensions, which preferably contain 1–200 mg of active ingredient per dosage unit, and are also rectally administered to treat diseases of the internal organs, in which leukotrienes play an important role, such as, e.g., allergic diseases of the intestinal tract, such as colitis ulcerosa and colitis granulomatosa.

Furthermore, the new leukotriene-B$_4$-antagonists are suitable for treating multiple sclerosis and symptoms of shock.

In these forms of administration, the new LTB$_4$ antagonists, in addition to the treatment of diseases of the internal organs with inflammatory processes, are also suitable for the treatment of diseases with increased growth and the formation of cells in which leukotrienes play an important role. Examples are leukemia (increased growth of white blood cells) or arteriosclerosis (increased growth of unstriped muscle cells of blood vessels).

The new pyridine derivatives can also be used in combination, such as, e.g., with lipoxygenase inhibitors, cyclooxygenase inhibitors, prostacyclin agonists, thromboxane antagonists, leukotriene-$D_4$-antagonists, leukotriene-$E_4$-antagonists, leukotriene-$F_4$-antagonists, phosphodiesterase inhibitors, calcium antagonists, PAF antagonists, glucocorticoids or other known forms of treatment of the respective diseases.

The following embodiments are used for a more detailed explanation of the process according to the invention and the process products obtained in this connection.

EXAMPLE 1

3-{[6-(4-Methoxyphenyl)-(5E)-5-hexenyloxy]-2-pyridiyl}-propionic acid

A. 152.6 g of potassium carbonate and 15.3 g of cesium carbonate are added to a solution of 122 g of 3-hydroxy-2-iodopyridine and 65.7 ml of benzyl bromide in 1.5 l of dimethylformamide, and the suspension is stirred under argon atmosphere for 20 hours at room temperature. The reaction mixture is filtered, the filter residue is washed with dichloromethane, the filtrate is concentrated by evaporation, and the residue is chromatographed on silica gel with hexane/10–20% ethyl acetate. 146.3 g of 3-benzyloxy-2-iodopyridine is obtained as oil.

IR(CHCl$_3$): 2980, 1552, 1438, 1402, 1371, 1067, 1002, 908 cm$^{-1}$.

B. 5.2 g of palladium(II) acetate, 77.8 g of potassium carbonate and 72.5 g of tetrabutylammonium bromide are added to a solution of 70 g of 3-benzyloxy-2-iodopyridine and 39.8 ml of acrylic acid methyl ester in 120 ml of dimethylformamide, and the suspension is stirred under argon atmosphere for 10 hours at 100° C. (bath temperature). The reaction mixture is concentrated by evaporation in a vacuum, the residue is added to water and shaken out with ethyl acetate. The organic phase is washed three times with water and once with saturated common salt solution, dried with sodium sulfate and concentrated by evaporation. The crude product is chromatographed on silica gel with hexane/10–25% ethyl acetate. 48.2 g of 3-(3-benzyloxy-2-pyridyl)-(2E)-2-propenoic acid methyl ester is obtained as oil.

IR(CHCl$_3$): 2955, 1708, 1640, 1577, 1440, 1310, 1167, 1110, 988 cm$^{-1}$.

C. In an autoclave, a solution of 11.5 g of 3-(3-benzyloxy-2-pyridyl)-(2E)-2-propenoic acid methyl ester in 125 ml of methanol is hydrogenated in the presence of 1.15 g of 10% palladium catalyst on activated carbon at an initial pressure of 32 bars for 2 hours at room temperature. The reaction mixture is filtered, the filter residue is washed with methanol and the filtrate is concentrated by evaporation. 6.8 g of 3-(3-hydroxy-2-pyridyl)-propionic acid methyl ester of melting point 94°–96° C. is obtained.

IR(CHCl$_3$): 2955, 1710, 1600, 1580, 1444, 1320, 1285, 1172, 1108, 1040, 986, 953, 912, 860 cm$^{-1}$.

D. 1.02 g of cesium carbonate is added to a solution of 300 mg of 3-(3-hydroxy-2-pyridyl)-propionic acid methyl ester and 450 mg of (1E)-6-bromo-1-(4-methoxyphenyl)-1-hexene in 6 ml of dimethylformamide, and the suspension is stirred under argon atmosphere for 20 hours at room temperature. The reaction mixture is filtered, the filter residue is washed with dichloromethane and the filtrate is concentrated by evaporation. The residue is added to water, shaken out with ethyl acetate, the organic phase is washed with saturated common salt solution, dried with sodium sulfate and concentrated by evaporation. The crude product is purified by high-pressure liquid chromatography on reversed-phase silica gel (Nova-Pak HR C18) with methanol/water=8/2. 280 mg of 3-{3-[6-(4-methoxyphenyl)-(5E)-5-hexenyloxy]-2-pyridyl}-propionic acid methyl ester is obtained as colorless oil.

IR(KBr): 2938, 2840, 1745, 1610, 1590, 1575, 1512, 1450, 1285, 1246, 1204, 1160, 1119, 1040, 960, 840, 810 cm$^{-1}$.

The production of (1E)-6-bromo-1-(4-methoxyphenyl)-1-hexene, used in example 1 D, is described in German Patent Application P 40 28 866.

E. A solution of 130 mg of 3-{3-[6-(4-methoxyphenyl)-(5E)-5-hexenyloxy]-2-pyridyl}-propionic acid methyl ester in 6.5 ml of methanol is mixed with 6.5 ml of 2n sodium hydroxide solution and stirred for 20 hours at room temperature. The methanol is removed in a vacuum, the alkaline solution is acidified to pH 5 with 2n sulfuric acid, shaken out with ethyl acetate, the organic phase is dried on sodium sulfate and concentrated by evaporation. 107 mg of the title compound is obtained as colorless oil.

IR(KBr): 2940, 1713, 1608, 1578, 1575, 1512, 1447, 1285, 1249, 1228, 1180, 1119, 1072, 1033, 965, 844, 810 cm$^{-1}$.

EXAMPLE 2

3-{3-[3-(4-Acetyl-3-methoxy-2-propylphenoxy)-propoxy]-2-pyridyl}-propionic acid

A. 1.34 g of potassium carbonate is added to a solution of 764 mg of 3-(3-hydroxy-2-pyridyl)-propionic acid methyl ester and 2 g of 2-hydroxy-4-(3-iodopropoxy)-3-propylacetophenone (J. Med. Chem. 1989, 32, 1145) in 33 ml of dimethylformamide, and the suspension is stirred under argon atmosphere for 6½ hours at 70° C. The reaction mixture is filtered, the filter residue is washed with ethyl acetate, and the filtrate is concentrated by evaporation. The residue is added in water, shaken out with ethyl acetate, the organic phase is washed with saturated common salt solution, dried with sodium sulfate and concentrated by evaporation. The crude product is chromatographed on silica gel with hexane/0–20% ethyl acetate. 1.12 g of 3-{3-[3-(4-acetyl-3-hydroxy-2-propylphenoxy)-propoxy]-2-pyridyl}-propionic acid methyl ester of melting point 85°–87° C. is obtained.

IR(CHCl$_3$): 2950, 2865, 1725, 1623, 1442, 1368, 1266, 1115, 1055, 985 cm$^{-1}$.

B. Under the conditions of example 2 A, 600 mg of 3-{3-[3-(4-acetyl-3-hydroxy-2-propylphenoxy)-propoxy]-2-pyridyl}-propionic acid methyl ester in the presence of 940 mg of cesium carbonate instead of potassium carbonate is reacted with 205 mg of iodomethane, worked up, and the crude product is chromatographed on silica gel with hexane/0–10% ethyl acetate. 570 mg of 3-{3-[3-(4-acetyl-3-methoxy-2-propylphenoxy)-propoxy]-2-pyridyl}-propionic acid methyl ester is obtained as oil.

IR(Film): 2950, 2865, 1730, 1668, 1585, 1440, 1404, 1352, 1260, 1210, 1110, 1004, 990, 793 cm$^{-1}$.

C. A solution of 200 mg of 3-{3-[3-(4-acetyl-3-methoxy-2-propylphenoxy)-propoxy]-2-pyridyl}-propionic acid methyl ester in 1 ml of methanol is mixed with 1.8 ml of 2n sodium hydroxide solution and stirred for 3 hours at 50° C. The reaction solution is worked up analogously to example 1E and 148 mg of the title compound is thus obtained as light yellow oil.

IR(Film): 2960, 2930, 2870, 1727, 1670, 1586, 1445, 1410, 1354, 1268, 1212, 1185, 1113, 1055, 800 cm$^{-1}$.

EXAMPLE 3

3-{6-Iodo-3-[6-(4-methoxyphenyl)-(5E)-5-hexenyloxy]-2-pyridyl}-propionic acid

A. A solution of 15 g of 3-(3-hydroxy-2-pyridyl)-propionic acid methyl ester in 250 ml of methanol is mixed with 12.4 g of sodium iodide, cooled to 15° C., and 74 ml of aqueous sodium hypochlorite solution (6.5% active chlorine) is instilled. The yellow suspension is concentrated by evaporation, the residue is taken up in water, acidified to pH 4 with 2n sulfuric acid and shaken out with ethyl acetate. The organic phase is washed with 10% sodium thiosulfate solution, dried with sodium sulfate, concentrated by evaporation and the residue is chromatographed on silica gel with hexane/0–50% ethyl acetate. 8.3 g of 3-(3-hydroxy-6-iodo-2-pyridyl)-propionic acid methyl ester of melting point 145°–148° C. is obtained.

IR(CHCl$_3$): 2958, 1710, 1590, 1435, 1410, 1370, 1260, 1172, 1112, 1095, 984 cm$^{-1}$.

B. Under the conditions of example 1 D, 850 mg of 3-(3-hydroxy-6-iodo-2-pyridyl)-propionic acid methyl ester is reacted with 612 mg of (1E)-6-bromo-1-(4-methoxyphenyl)-1-hexene, worked up, and the crude product is chromatographed on silica gel with hexane/0–5% ethyl acetate. 773 mg of 3-{6-iodo-3-[6-(4-methoxyphenyl)-(5E)-5-hexenyloxy]-2-pyridyl}-propionic acid methyl ester is obtained as colorless oil.

IR(CHCl$_3$): 2940, 1725, 1604, 1570, 1505, 1431, 1171, 1118, 1100, 1025, 962 cm$^{-1}$.

C. A solution of 460 mg of 3-{6-iodo-3-[6-(4-methoxyphenyl-(5E)-5-hexenyloxy]-2-pyridyl}-propionic acid methyl ester in 5 ml of methanol and 5 ml of tetrahydrofuran is mixed with 3 ml of 1n sodium hydroxide solution and stirred for 20 hours at room temperature. The methanol is distilled off in a vacuum, the alkaline solution is acidified to pH 3 with 2n sulfuric acid, shaken out with ethyl acetate, the organic phase is dried on sodium sulfate and concentrated by evaporation. 446 mg of the title compound is obtained as light yellow solid of melting point 95°–97° C.

IR(CHCl$_3$): 2940, 1720, 1608, 1572, 1510, 1433, 1175, 1123, 1100, 1028, 965 cm$^{-1}$.

EXAMPLE 4

3-{6-Acetyl-3-[6-(4-methoxyphenyl)-(5E)-5-hexenyloxy]-2-pyridyl}-propionic acid

A. A solution of 495 mg of 3-{6-iodo-3-[6-(4-methoxyphenyl-(5E)-5-hexenyloxy]-2-pyridyl}-propionic acid methyl ester and 397 mg of ethoxyvinyltributyltin in 2 ml of toluene is mixed with 30 mg of bis-triphenylphosphine-palladium(II) chloride and heated for six hours with stirring to 110° C. The reaction mixture is filtered on diatomaceous earth, the filter residue is washed with diethyl ether, the filtrate is mixed with 1.5 ml of 2n hydrochloric acid and stirred for 4 hours at room temperature. The organic phase is separated, dried with sodium sulfate and concentrated by evaporation. 95 mg of 3-{6-acetyl-3-[6-(4-methoxyphenyl)-(5E)-5-hexenyloxy]-2-pyridyl}-propionic acid methyl ester is obtained as oil.

IR(CHCl$_3$): 2930, 1725, 1680, 1604, 1568, 1506, 1450, 1359, 1171, 1118, 1097, 1028, 963, 830 cm$^{-1}$.

B. Under the conditions of example 1 E, a solution of 90 mg of 3-{6-acetyl-3-[6-(4-methoxyphenyl-(5E)-5-hexenyloxy]-2-pyridyl}-propionic acid methyl ester in 1 ml of methanol is saponified with 0.7 ml of 2n sodium hydroxide solution and worked up. 73 mg of the title compound of melting point 89°–90° C. is obtained.

IR(KBr): 2970, 2925, 1710, 1688, 1610, 1572, 1518, 1460, 1362, 1325, 1254, 1222, 1179, 1122, 1042, 963, 840, 820, 598 cm$^{-1}$.

EXAMPLE 5

5-{2-(2-Carboxyethyl)-3-[6-4-methoxyphenyl)-(5E)-5-hexenyloxy]-6-pyridyl}-4-pentynoic acid A. 11 mg of bis-triphenylphosphine-palladium(II) chloride and 1.5 mg of copper(I) iodide are added to a solution of 300 mg of 3-{6-iodo-3-[6-(4-methoxyphenyl)-(5E)-5-hexenyloxy]-2-pyridyl}-propionic acid methyl ester and 68 mg of 4-pentynoic acid methyl ester in 5 ml of triethylamine, and the mixture is stirred for 20 hours at room temperature. The reaction mixture is filtered, the filter residue is washed with ethyl acetate and the filtrate is concentrated by evaporation. The residue is taken up in water, shaken out with ethyl acetate, dried on sodium sulfate and concentrated by evaporation. The crude product is chromatographed on silica gel with hexane/0–10% ethyl acetate and for complete purification subjected to high-pressure liquid chromatography on reversed-phase silica gel (Nova-Pak HR C18) with acetonitrile/water=75/25. 280 mg of 5-{2-(2-methoxycarbonylethyl)-3-[6-(4-methoxyphenyl)-(5E)-5-hexenyloxy]-6-pyridyl}-4-pentynoic acid methyl ester is obtained as colorless oil.

IR(CHCl$_3$): 2925, 2850, 1730, 1607, 1572, 1509, 1450, 1438, 1364, 1300, 1172, 1114, 1029, 964 cm$^{-1}$.

B. Under the conditions of example 1 E, a solution of 90 mg of 5-{2-(2-methoxycarbonylethyl)-3-[6-4-methoxyphenyl-(5E)-5-hexenyloxy]-6-pyridyl}-4-pentynoic acid methyl ester in 3 ml of methanol and 1 ml of tetrahydrofuran is saponified with 3 ml of 2n sodium hydroxide solution and worked up. 65 mg of the title compound of melting point 89°–91° C. is obtained.

IR(KBr): 3420 (broad), 2930, 1732, 1705, 1602, 1570, 1508, 1456, 1305, 1242, 1175, 1120, 1030, 805 cm$^{-1}$.

EXAMPLE 6

3-{6-[2-(3-Carboxyphenyl)-ethinyl]-3-[6-(4-methoxyphenyl)-(5E)-5-hexenyloxy]-2-pyridyl}-propionic acid A. Under the conditions of example 5 A, 1 g of 3-{6-iodo-3-[6-(4-methoxyphenyl)-(5E)-5-hexenyloxy]-2-pyridyl}-propionic acid methyl ester is reacted with 320 mg of 3-ethinylbenzoic acid methyl ester, worked up, and the crude product is chromatographed on silica gel with hexane/0–15% ethyl acetate. 835 mg of 3-{6-[2-(3-methoxycarbonylphenyl)-ethinyl]-3-[6-(4-methoxyphenyl)-(5E)-5-hexenyloxy]-2-pyridyl}-propionic acid methyl ester is obtained as oil.

IR(CHCl$_3$): 2943, 1718, 1604, 1571, 1505, 1448, 1285, 1170, 1102, 1028, 962 cm$^{-1}$.

B. Under the conditions of example 3 C, 70 mg of 3-{6-[2-(3-methoxycarbonylphenyl)-ethinyl]-3-[6-(4-methoxyphenyl)-(5E)-5-hexenyloxy]-2-pyridyl}-propionic acid methyl ester in 3 ml of methanol is saponified with 3 ml of 2n sodium hydroxide solution and worked up. 56 mg of the title compound of melting point 76°–79° C. is obtained.

IR(KBr): 2925, 2848, 2220, 1705, 1690, 1608, 1575, 1515, 1548, 1358, 1290, 1242, 1180, 1117, 1040, 828, 818, 758 cm$^{-1}$.

EXAMPLE 7

3-{6-2-(4-Carboxyphenyl)-ethinyl]-3-[6-(4-methoxyphenyl)-(5E)-5-hexenyloxy]-2-pyridyl}-propionic acid A. Under the conditions of example 5 A, 1 g of 3-{6-iodo-3-[6-(4-methoxyphenyl)-(5E)-5-hexenyloxy]-2-pyridyl}-propionic acid methyl ester is reacted with 384 mg of 4-ethinylbenzoic acid methyl ester, worked up, and the crude product is chromatographed on silica gel with hexane/ 0–7% ethyl acetate. 670 mg of 3-{6-[2-(4-methoxycarbonylphenyl)-ethinyl]-3-[6-(4-methoxyphenyl)-(5E)-5-hexenyloxy]-2-pyridyl}-propionic acid methyl ester is obtained as oil.

IR(CHCl$_3$): 2943, 2835, 2200, 1715, 1602, 1568, 1504, 1445, 1273, 1170, 1108, 1013, 963, 852, 820 cm$^{-1}$.

B. Under the conditions of example 3 C, 600 mg of 3-{6-[2-(4-methoxycarbonylphenyl)-ethinyl]-3-[6-(4-methoxyphenyl)-(5E)-5-hexenyloxy]-2-pyridyl}-propionic acid methyl ester in 4 ml of methanol and 2 ml of tetrahydrofuran is saponified with 4 ml of 2n sodium hydroxide solution and worked up. 548 mg of the title compound of melting point 153°–156° C. is obtained.

IR(KBr): 2930, 2200, 1718, 1674, 1600, 1565, 1507, 1450, 1420, 1312, 1285, 1240, 1172, 1110, 964, 860, 770 cm$^{-1}$.

EXAMPLE 8

3-{6-[2-(4-Carboxyphenyl)-ethinyl]-3-[6-(4-methoxyphenyl)-(5E)-5-hexenyloxy]-2-pyridyl }-propionic acid, bis-tris-(hydroxymethyl)-aminomethane salt A solution of 200 mg of 3-{6-[2-(4-carboxyphenyl)-ethinyl]-3-[6-(4-methoxyphenyl)-(5E)-5-hexenyloxy]-2-pyridyl}-propionic acid in 24 ml of acetonitrile is heated to 80° C. and mixed with 0.152 ml of a solution of 8.225 g of tris-(hydroxymethyl)aminomethane in 15 ml of water. The mixture is stirred for one hour at 80° C., one hour at 55° C., three hours at 45° C. and 48 hours at room temperature. The crystallizate is suctioned off and dried in a vacuum. 218 mg of the title compound of melting point 108°–110° C. is obtained.

IR(KBr): 3300 (broad), 2930, 2205, 1603, 1575, 1508, 1450, 1385, 1245, 1172, 1110, 1060, 1028, 965, 785 cm$^{-1}$.

EXAMPLE 9

3-{6-[2-(4-Carboxyphenyl)-ethinyl]-3-decyloxy-2-pyridyl}-propionic acid

A. Under the conditions of example 5 A, 6.3 g of 3-(3-hydroxy-6-iodo-2-pyridyl)-propionic acid methyl ester is reacted with 3.28 g of 4-ethinylbenzoic acid methyl ester, worked up, and the crude product is chromatographed on silica gel with hexane/0–50% ethyl acetate. 4.1 g of 3-{3-hydroxy-6-[2-(4-methoxycarbonylphenyl)-ethinyl]-2-pyridyl}-propionic acid methyl ester of melting point 173°–177° C. is obtained.

IR(CHCl$_3$): 2950, 1718, 1710, 1604, 1452, 1435, 1365, 1300, 1277, 1104, 1015, 965, 855, 835 cm$^{-1}$.

B. Under the conditions of example 1 D, 500 mg of 3-{3-hydroxy-6-[2-(4-methoxycarbonylphenyl)-ethinyl]-2-pyridyl}-propionic acid methyl ester is reacted with 358 mg of 1-decyl bromide and worked up. 531 mg of 3-{6-[2-(4-methoxycarbonylphenyl)-ethinyl]-3-decyloxy-2-pyridyl}-propionic acid methyl ester of melting point 88°–90° C. is obtained.

IR(CHCl$_3$): 2930, 2860, 1720, 1608, 1575, 1450, 1310, 1279, 1112, 1020, 860 cm$^{-1}$.

C. Under the conditions of example 3 C, 372 mg of 3-{6-[2-(4-methoxycarbonylphenyl)-ethinyl]-3-decyloxy-2-pyridyl}-propionic acid methyl ester in 1.6 ml of methanol and 5 ml of tetrahydrofuran is saponified with 2.2 ml of in sodium hydroxide solution and worked up. 190 mg of the title compound of melting point 167° C. is obtained.

IR(KBr): 2920, 2850, 2210, 1708, 1690, 1605, 1672, 1450, 1420, 1285, 1243, 1171, 1112, 1019, 860, 832, 770 cm$^{-1}$.

EXAMPLE 10

3-{6-[2-(4-Carboxyphenyl)-ethinyl]-3-[3-(4-acetyl-3-methoxy-2-propylphenoxy)-propoxy]-2-pyridyl}-propionic acid A. Under the conditions of example 2 A, 1 g of 3-{3-hydroxy-6-[2-(4-methoxycarbonylphenyl)-ethinyl]-2-pyridyl}-propionic acid methyl ester is reacted with 1.39 g of 2-hydroxy-4-(3-iodopropoxy)-3-propylacetophenone, worked up, and the crude product is chromatographed on silica gel with hexane/0–10% ethyl acetate. 1.48 g of 3-{6-[2-(4-methoxycarbonylphenyl)-ethinyl]-3-[3-(4-acetyl-3-hydroxy-2-propylphenoxy)-propoxy]-2-pyridyl}-propionic acid methyl ester of melting point 71°–73° C. is obtained.

IR(CHCl$_3$): 2960, 2878, 1722, 1675, 1627, 1608, 1575, 1500, 1450, 1370, 1270, 1116, 1060, 1018, 858, 826 cm$^{-1}$.

B. Under the conditions of example 2 B, 1.4 g of 3-{6-[2-(4-methoxy-carbonylphenyl)-ethinyl]-3-[3-(4-acetyl-3-hydroxy-2-propylphenoxy-propoxy]-2-pyridyl}-propionic acid methyl ester is reacted with 345 mg of iodomethane and worked up. 1.28 g of 3-{6-[2-(4-methoxycarbonylphenyl)-ethinyl]-3-[3-(4-acetyl-3-methoxy-2-propylphenoxy-propoxy]-2-pyridyl}-propionic acid methyl ester is obtained as yellow oil.

IR(Film): 2955, 2875, 2218, 1723, 1672, 1604, 1588, 1450, 1410, 1360, 1274, 1112, 1058, 1018, 858, 770, 695 cm$^{-1}$.

C. Under the conditions of example 3 C, 1.2 g of 3-{6-[2-(4-methoxycarbonyl-phenyl)-ethinyl]-3-[3-(4-acetyl-3-methoxy-2-propylphenoxy)-propoxy]-2-pyridyl}-propionic acid methyl ester in 20 ml of methanol is saponified with 14 ml of 2n sodium hydroxide solution and worked up. 1.1 g of the title compound of melting point 134°–135° C. is obtained.

IR(KBr): 2960, 2880, 2215, 1705, 1680, 1608, 1590, 1458, 1415, 1360, 1275, 1222, 1120, 1060, 1020, 860, 830, 675 cm$^{-1}$.

EXAMPLE 11

3-{6-[2-(4-Carboxyphenyl)-ethinyl]-3-[(3RS)-3,7-dimethyl-6-octenyloxy]-2-pyridyl}-propionic acid A. Under the conditions of example 1 D, 500 mg of 3-{3-hydroxy-6-[2-(4-methoxycarbonylphenyl)-ethinyl]-2-pyridyl}-propionic acid methyl ester is reacted with 354 mg of 1-bromo-(3RS)-3,7-dimethyl-6-octene, worked up, and the crude product is chromatographed on silica gel with hexane/0–10% ethyl acetate. 522 mg of 3-{6-[2-(4-methoxycarbonylphenyl)-ethinyl]-3-[(3RS)-3,7-dimethyl-6-octenyloxy]-2-pyridyl}-propionic acid methyl ester is obtained as yellow oil.

IR(Film): 2950, 2920, 2218, 1722, 1604, 1572, 1510, 1448, 1310, 1172, 1110, 1015, 858, 830, 770, 695 cm$^{-1}$.

B. Under the conditions of example 3 C, 500 mg of 3-{6-[2-(4-methoxy-carbonylphenyl)-ethinyl]-3-[(3RS)-3, 7-dimethyl-6-octenyloxy]-2-pyridyl}-propionic acid methyl ester in 10 ml of methanol is saponified with 7.2 ml of 2n sodium hydroxide solution and worked up. 437 mg of the title compound of melting point 154°–156° C. is obtained.

IR(KBr): 2920, 2215, 1718, 1685, 1607, 1575, 1458, 1422, 1280, 1252, 1200, 1175, 1120, 1002, 860, 840, 770 cm$^{-1}$.

EXAMPLE 12

3-{3-[6-(4-Methoxyphenyl)-(5E)-5-hexenyloxy]-6-(2-phenylethinyl)-2-pyridyl}-propionic acid methyl ester A. Under the conditions of example 5 A, 500 mg of 3-{6-iodo-3-[6-(4-methoxyphenyl)-(5E)-5-hexenyloxy]-2-pyridyl}-propionic acid methyl ester is reacted with 102 mg of phenylacetylene, worked up, and the crude product is chromatographed on silica gel with hexane/0–7% ethyl acetate. 265 mg of 3-{3-[6-(4-methoxyphenyl)-(5E)-5-hexenyloxy]-6-(2-phenylethinyl)-2-pyridyl}-propionic acid methyl ester is obtained as oil.

IR(Film): 2955, 2840, 1738, 1605, 1575, 1510, 1450, 1282, 1245, 1175, 1115, 1035, 965, 825, 760, 690 cm$^{-1}$.

B. Under the conditions of example 3 C, 260 mg of 3-{3-[6-(4-methoxyphenyl)-(5E)-5-hexenyloxy]-6-(2-phenylethinyl)-2-pyridyl}-propionic acid-methyl ester in 2.5 ml of methanol and 2.5 ml of tetrahydrofuran is saponified with 5 ml of 1n sodium hydroxide solution and worked up. 201 mg of the title compound of melting point 121°–123° C. is obtained.

IR(KBr): 2950, 2920, 2840, 2220, 1710, 1605, 1577, 1510, 1450, 1350, 1285, 1253, 1220, 1180, 1113, 962, 760 cm$^{-1}$.

EXAMPLE 13

3-{6-[2-(3-carboxyphenyl)-ethinyl]-3-[6-(4-methoxyphenyl)-(5E)-5-hexenyloxy]-2-pyridyl}-propionic acid, bis-tris-hdyroxymethyl)-aminomethane salt Under the conditions of example 8, 170 mg of 3-{6-[2-(3-carboxyphenyl)-ethinyl]-3-[6-(4-methoxyphenyl)-(5E)-5-hexenyloxy]-2-pyridyl}-propionic acid is reacted with tris-(hydroxymethyl)-aminomethane and worked up. 250 mg of the title compound of melting point 104°–108° C. is obtained.

IR(KBr): 3250 (broad), 2940, 2220, 1640, 1604, 1580, 1550, 1510, 1450, 1390, 1300, 1244, 1183, 1115, 1060, 960, 845, 808, 760, 680 cm$^{-1}$.

EXAMPLE 14

3-{6-[2-(4-Carboxyphenyl)-ethyl]-3-[6-(4-methoxyphenyl)-(5E)-5-hexenyloxy]-2-pyridyl}-propionic acid A. A solution of 300 mg of 3-{3-hydroxy-6-[2-(4-methoxycarbonylphenyl)-ethinyl]-2-pypridyl}-propionic acid methyl ester in 3 ml of methanol is hydrogenated in the presence of 30 mg of 10% palladium catalyst on activated carbon at normal pressure and room temperature until two equivalents of hydrogen are taken up. The reaction mixture is filtered, the filter residue is washed with methanol and the filtrate is concentrated by evaporation. 290 mg of 3-{6-[2-(4-methoxycarbonylphenyl)-ethyl]-3-hydroxy-2-pyridyl}-propionic acid methyl ester of melting point 137°–139° C. is obtained.

IR(CHCl$_3$): 3320 (broad), 2950, 1710, 1612, 1468, 1440, 1370, 1284, 1180, 1110, 1022, 970 cm$^{-1}$.

B. Under the conditions of example 1 D, 280 mg of 3-{6-[2-(4-methoxy-carbonylphenyl)-ethyl]-3-hydroxy-2-pyridyl}-propionic acid methyl ester is reacted with 220 mg of (1E)-6-bromo-1-(4-methoxyphenyl)-1-hexene, worked up, and the crude product is chromatographed on silica gel with hexane/0–10% ethyl acetate. 230 mg of 3-{6-[2-(4-methoxycarbonylphenyl)-ethyl]-3-[6-(4-methoxyphenyl)-(5E)-5-hexenyloxy]-2-pyridyl}-propionic acid methyl ester of melting point 59°–61° C. is obtained.

IR(CHCl$_3$): 2945, 1715, 1608, 1580, 1510, 1460, 1435, 1283, 1175, 1115, 1020, 968 cm$^{-1}$.

C. Under the conditions of example 3 C, 210 mg of 3-{6-[2-(4-methoxy-carbonylphenyl)-ethyl]-3-[6-(4-methoxyphenyl)-(5E)-5-hexenyloxy]-2-pyridyl}-propionic acid methyl ester in 5.4 ml of methanol and 1 ml of tetrahydrofuran is saponified with 2.7 ml of 2n sodium hydroxide solution and worked up 153 mg of the title compound of melting point 135°–138° C. is obtained.

IR(KBr): 3430 (broad), 2950, 1695, 1608, 1580, 1510, 1460, 1420, 1240, 1178, 1117, 1038, 965, 842, 820, 760 cm$^{-1}$.

EXAMPLE 15

1,10-Bis-{2-(2-carboxyethyl)-6-[2-(4-carboxyphenyl)-ethinyl]-3-pyridyloxy}-decane A. Under the conditions of example 1 D, 500 mg of 3-{6-[2-(4-methoxy-carbonylphenyl)-ethinyl]-3-hydroxy-2-pyridyl}-propionic acid methyl ester is reacted with 221 mg of 1,10-dibromodecane, worked up, and the crude product is absorptively precipitated with methanol. After the suctioning off and drying of the crystallizate, 420 mg of 1,10-bis-{2-(2-methoxycarbonylethyl)-6-[2-(4-methoxycarbonylphenyl)-ethinyl]-3-pyridyloxy)-decane of melting point 143°–145° C. is obtained.

IR(CHCl$_3$): 2940, 2860, 1722, 1608, 1574, 1452, 1301, 1280, 1112, 1020, 860 cm$^{-1}$.

B. Under the conditions of example 3 C, 410 mg of 1,10-bis-{2-(2-methoxycarbonylethyl)-6-[2-(4-methoxycarbonylphenyl)-ethinyl]-3-pyridyl-oxy}-decane in 11 ml of methanol and 25 ml of tetrahydrofuran is saponified with 5.3 ml of 2n sodium hydroxide solution and worked up. The crude product is absorptively precipitated with methanol, the crystallizate is suctioned off and dried in a vacuum. 360 mg of the title compound of melting point>300° C. is obtained.

IR(KBr): 3430 (broad), 2930, 2850, 2220, 1700, 1605, 1575, 1450, 1420, 1283, 1255, 1165, 1117, 1018, 860, 830, 770, 678, 620 cm$^{-1}$.

EXAMPLE 16

5-{2-(2-Carboxyethyl)-3-[6-(4-methoxyphenyl)-(5E)-5-hexenyloxy]-6-pyridyl}-5-oxopentanoic acid A. Under the conditions of example 1 D, 10 g of 3-hydroxy-2-iodo-6-methylpyridine is reacted with 2.7 ml of iodomethane and worked up. 10.5 g of 2-iodo-3-methoxy-6-methylpyridine of melting point 45°–50° C. is obtained.

IR(CHCl$_3$): 2970, 2920, 2820, 1586, 1554, 1460, 1425, 1360, 1284, 1254, 1139, 1070, 1012, 990, 852 cm$^{-1}$.

B. A solution of 22 g of 2-iodo-3-methoxy-6-methylpyridine in 880 ml of water is mixed at 70° C. for 5 hours in portions with 70 g of potassium permanganate. Then, the reaction mixture is stirred for 16 hours at 80°–90° C., hot-filtered, the filter residue is washed with a hot mixture of methanol/water=1/l, the filtrate is concentrated by evaporation to a half, shaken out with ethyl acetate, and the water phase is acidified to pH 2 with 2n hydrochloric acid. The crystallizate is suctioned off and dried in a vacuum. 11.5 g of 2-iodo-3-methoxy-pyridine-6-carboxylic acid of melting point 213°–216° C. is obtained.

IR(CHCl$_3$): 3330 (broad), 3030, 3005, 2970, 1760, 1560, 1460, 1420, 1377, 1355, 1260, 1121, 1065, 1010, 925, 843 cm$^{-1}$.

C. Under the conditions of example 1 D, 9.8 g of 2-iodo-3-methoxy-pyridine-6-carboxylic acid is reacted with 2.5 ml of iodomethane and worked up. 7.4 g of 2-iodo-3-methoxypyridine-6-carboxylic acid methyl ester of melting point 175°–178° C. is obtained.

IR(CHCl$_3$): 2992, 2950, 2842, 1719, 1556, 1460, 1440, 1420, 1372, 1327, 1270, 1137, 1063, 1008, 970, 842, 616 cm$^{-1}$.

D. 40 ml of a 25% solution of diisobutylaluminum hydride in toluene is added drop by drop to a solution of 7 g of 2-iodo-3-methoxypyridine-6-carboxylic acid methyl ester in 95 ml of toluene and 50 ml of tetrahydrofuran at −70° C. The reaction mixture is stirred for 30 minutes at −70° C., heated to −5° C. within two hours and stirred for 2 hours at this temperature. The reaction mixture is cooled to −70° C., mixed in succession with 20 ml of isopropanol and 20 ml of water and stirred for three hours at room temperature. The precipitate is suctioned off on diatomaceous earth, the filter residue is washed with dichloromethane and the filtrate is concentrated by evaporation. 6.54 g of 6-hydroxymethyl-2-iodo-3-methoxypyridine of melting point 106°–108° C. is obtained.

IR(CHCl$_3$): 3600, 3400 (broad), 2970, 2920, 2820, 1585, 1555, 1460, 1425, 1360, 1284, 1135, 1070, 1010, 820 cm$^{-1}$.

E. 175 g of manganese dioxide is added to a solution of 29 g of 6-hydroxymethyl-2-iodo-3-methoxypyridine in 600 ml of toluene, and the suspension is heated with stirring and refluxed for three hours on a water separator. The reaction mixture is filtered, the filter residue is washed with dichloromethane, the filtrate is dried on sodium sulfate and concentrated by evaporation. The crude product is chromatographed on silica gel with hexane/0–25% ethyl acetate. 12.9 g of 2-iodo-3-methoxypyridine-6-aldehyde of melting point 118°–121° C. is obtained.

IR(CHCl$_3$): 2985, 2920, 2830, 1698, 1550, 1455, 1417, 1380, 1312, 1270, 1120, 1058, 1003, 865, 825 cm$^{-1}$.

F. 680 mg of zinc foil cut into small sections (Aldrich 0.25 mm thickness, 99.999%) in 1 ml of absolute tetrahydrofuran is heated to 65° C. with 80 mg of 1,2-dibromoethane for 1 minute, cooled to 25° C., mixed with 40 μl of chlorotrimethylsilane and stirred for 15 minutes. A solution of 2.3 g of 3-iodobutyric acid methyl ester in 5 ml of absolute tetrahydrofuran is instilled in this activated zinc at 30° C., and the mixture is stirred for 16 hours at 35°–40° C. 4.3 ml of the thus obtained 2-methoxycarbonylpropylzinc iodide solution is instilled at −20° C. in a solution of 430 mg of copper(I) dyanid and 430 mg of lithium chloride in 1 ml of tetrahydrofuran. The reaction mixture is stirred for 5 minutes at 0° C., cooled again to −20° C., mixed with a solution of 1.1 g of 2-iodo-3-methoxypyridine-6-aldehyde in 2 ml of tetrahydrofuran and 2 ml of dichloromethane and 1.9 ml of boron trifluoride-ethyl ether complex, stirred for three hours at 0° C. and 20 hours at room temperature. The reaction mixture is poured in saturated ammonium chloride solution, the precipitate is suctioned off on diatomaceous earth, the filter residue is washed with ethyl acetate, the organic phase is separated and the water phase is also shaken out three times with ethyl acetate. The organic phase is dried on sodium sulfate, concentrated by evaporation and the crude product is chromatographed on silica gel with hexane/0–20% ethyl acetate. 1.11 g of (5RS)-5-hydroxy-5-(2-iodo-3-methoxy-6-pyridyl)-pentanoic acid methyl ester is obtained as oil.

IR(Film): 3430 (broad), 2940, 2860, 1727, 1550, 1456, 1425, 1362, 1285, 1200, 1063, 1005, 825, 615 cm$^{-1}$.

G. Under the conditions of example 16 E, 9.98 g of (5RS)-5-hydroxy-5-(2-iodo-3-methoxy-6-pyridyl)-pentanoic acid methyl ester is reacted with 43 g of manganese dioxide for 6 hours, worked up, and the crude product is chromatographed on silica gel with hexane/0–35% ethyl acetate. 4.3 g of 5-(2-iodo-3-methoxy-6-pyridyl)-5-oxopentanoic acid methyl ester of melting point 111° C. is obtained.

IR(CHCl$_3$): 2990, 2940, 2842, 1724, 1690, 1552, 1455, 1418, 1360, 1303, 1124, 1060, 1005, 827 cm$^{-1}$.

H. 244 mg of palladium acetate, 3.66 g of potassium carbonate and 3.4 g of tetrabutylammonium bromide are added to a solution of 3.87 g of 5-(2-iodo-3-methoxy-6-pyridyl)-5-oxopentanoic acid methyl ester and 1.87 ml of acrylic acid methyl ester in 10 ml of dimethylformamide, and the suspension is heated to 100° C. with stirring and under argon atmosphere for 5 hours. The solvent is removed in a vacuum, the residue is mixed with water, shaken out with ethyl acetate, the organic phase is dried on sodium sulfate and concentrated by evaporation. The crude product is chromatographed on silica gel with hexane/0–15% ethyl acetate. 1.89 g of 5-{3-methoxy-2-[2-methoxycarbonyl-(1E)-1-ethenyl-]-6-pyridyl}-5-oxopentanoic acid methyl ester of melting point 87°–89° C. is obtained.

IR(CHCl$_3$): 2943, 2840, 1715, 1688, 1640, 1565, 1460, 1433, 1362, 1312, 1274, 1165, 1102, 1010, 883 cm$^{-1}$.

I. Under the conditions of example 1 C, a solution of 1.89 g of 5-[3-methoxy-2-(2-methoxycarbonyl-(1E)-1-ethenyl)-6-pyridyl]-5-oxopentanoic acid methyl ester in 75 ml of methanol and 15 ml of tetrahydrofuran is hydrogenated in the presence 400 mg of 10% palladium catalyst and worked up. 1.9 g of 5-[3-methoxy-2-(2-methoxycarbonylethyl)-6-pyridyl]-(5RS)-5-hydroxypentanoic acid methyl ester is obtained as oil.

IR(Film): 3440 (broad), 2948, 2840, 1720, 1580, 1463, 1435, 1364, 1263, 1202, 1165, 1112, 1018, 988, 833 cm$^{-1}$.

J. 2.9 g of Collins reagent is added to a solution of 470 mg of 5-[3-methoxy-2-(2-methoxycarbonylethyl)-6-pyridyl]-(5RS)-5-hydroxypentanoic acid methyl ester in 50 ml of dichloromethane under argon atmosphere at 0° C., and the mixture is stirred for 2 hours at room temperature. Then, it is diluted with hexane, mixed with diatomaceous earth until paste formation, filtered on diatomaceous earth and rewashed with ethyl acetate. The filtrate is concentrated by evaporation, and the crude product is chromatographed on silica gel with hexane/0–10% ethyl acetate. 337 mg of 5-[3-methoxy-2-(2-methoxycarbonylethyl)-6-pyridyl]-5-oxopentanoic acid methyl ester of melting point 64°–66° C. is obtained.

IR(CHCl$_3$): 2950, 2840, 1725, 1685, 1568, 1460, 1434, 1259, 1110, 1015, cm$^{-1}$.

K. A solution of 330 mg of 5-[3-methoxy-2-(2-methoxycarbonylethyl)-6-pyridyl]-5-oxopentanoic acid methyl ester in 3 ml of 48% hydrobromic acid is refluxed for 13 hours. The hydrobromic acid is distilled off, the residue is dissolved in water, adjusted to pH 4 with concentrated ammonia solution, shaken out with ethyl acetate, the organic phase is dried on sodium sulfate and concentrated by evaporation. 190 mg of 5-[2-(2-carboxyethyl)-3-hydroxy-6-pyridyl]-5-oxopentanoic acid is obtained as crude product of melting point 134°–136° C. 180 mg of this crude product is dissolved in 5 ml of methanol with 60 mg of Amberlyst 15 and stirred for 16 hours at room temperature. The reaction mixture is filtered on diatomaceous earth, the filter residue is washed with ethyl acetate, the filtrate is concentrated by evaporation, and the crude product is chromatographed on silica gel with hexane/0–15% ethyl acetate. 75 mg of 5-[3-hydroxy-2-(2-methoxycarbonylethyl)-6-pyridyl]-5-oxopentanoic acid methyl ester is obtained as yellow oil.

IR(CHCl$_3$): 3300 (broad), 2945, 2840, 1730, 1680, 1590, 1568, 1433, 1412, 1283, 1094, 1020, 988, 835 cm$^{-1}$.

L. Under the conditions of example 1 D, 70 mg of 5-[3-hydroxy-2-(2-methoxycarbonylethyl)-6-pyridyl]-5-oxopentanoic acid methyl ester is reacted with 58 mg of (1E)-6-bromo-1-(4-methoxyphenyl)-1-hexene, worked up, and the crude product is chromatographed on silica gel with hexane/0–5% ethyl acetate. 52 mg of 5-{2-(2-methoxycarbonylethyl)-3-[6-(4-methoxyphenyl)-(5E)-5-hexenyloxy]-6-pyridyl}-5-oxopentanoic acid methyl ester is obtained as oil.

IR(CHCl$_3$): 2943, 1727, 1684, 1605, 1567, 1510, 1450, 1435, 1170, 1105, 1014, 965 cm$^{-1}$.

M. Under the conditions of example 3 C, 52 mg of 5-{2-(2-methoxycarbonyl-ethyl)-3-6-(4-methoxyphenyl)-(5E)-5-hexenyloxy]-6-pyridyl}-5-oxopentanoic acid methyl ester in 1.4 methanol is saponified with 0.5 ml of 2n sodium hydroxide solution and worked up. 30 mg of the title compound of melting point 99°–102° C. is obtained.

IR(KBr): 3420 (broad), 2940, 1705, 1695, 1607, 1572, 1515, 1458, 1335, 1248, 1220, 1380, 1110, 1038, 1012, 970, 846 cm$^{-1}$.

EXAMPLE 17

5-{2-(2-Carboxyethyl)-3-[6-(4-methoxyphenyl)-(5E)-5-hexenyloxy]-6-pyridyl}-(5RS)-5-hydroxypentanoic acid A solution of 20 mg of 5-{2-(2-carboxyethyl)-3-[6-(4-methoxyphenyl)-(5E)-5-hexenyloxy]-6-pyridyl}-5-oxopentanoic acid in 0.9 ml of dioxane and 0.1 ml of water is mixed with 6.5 mg of sodium borohydride and stirred for 2 hours at room temperature. The reaction mixture is mixed with ice water, acidified with glacial acetic acid, shaken out with dichloromethane, the organic phase is dried on sodium sulfate and concentrated by evaporation. The crude product is dissolved in 0.6 ml of methanol, 0.3 ml of 2n sodium hydroxide solution is added, and the mixture is stirred for 48 hours at room temperature. The reaction mixture is concentrated by evaporation, acidified to pH 3 with 2n sulfuric acid, shaken out with ethyl acetate, the organic phase is dried on sodium sulfate and concentrated by evaporation. 15 mg of the title compound is obtained as colorless oil.

IR(CHCl$_3$): 3610, 3440 (broad), 2970, 1715, 1605, 1585, 1564, 1510, 1440, 1410, 1155, 1172, 1040, 967, 928, 875 cm$^{-1}$.

EXAMPLE 18

3-{6-[2-(3-Carboxyphenyl)-(1E)-1-ethenyl]-3-[6-(4-methoxyphenyl)-(5E)-5-hexenyoxy]-2-pyridyl}-propionic acid A. Under the conditions of example 16 H, a solution of 20 g of 2-iodo-3-methoxypyridine-6-aldehyde in 100 ml of dimethylformamide is reacted with 33.5 ml of acrylic acid methyl ester in the presence of 1.73 g of palladium acetate, 26.1 g of potassium carbonate and 23.8 g of tetrabutylammonium bromide, worked up, and the crude product is chromatographed on silica gel with hexane/0–50% ethyl acetate. 11.66 g of 3-(6-formyl-3-methoxy-2-pyridyl)-(2E)-2-propenoic acid methyl ester of melting point 132°–134° C. is obtained.

IR(CHCl$_3$): 2945, 2840, 1720, 1700, 1641, 1564, 1463, 1435, 1315, 1305, 1270, 1165, 1103, 1014, 884 cm$^{-1}$.

B. Under the conditions of example 1 C, a solution of 11 g of 3-(6-formyl-3-methoxy-2-pyridyl)-(2E)-2-propenoic acid methyl ester in 140 ml of tetrahydrofuran and 40 ml of methanol in the presence of 1.2 g of 10% palladium catalyst is hydrogenated on activated carbon and worked up. 11 g of 3-(6-hydroxymethyl-3-methoxy-2-pyridyl)-propionic acid methyl ester is obtained as oily crude product, which is reacted under the conditions of example 16 E with 78 g of manganese dioxide for 2½ hours and is worked up. 8.92 g of 3-(6-formyl-3-methoxy-2-pyridyl)-propionic acid methyl ester of melting point 95°–97° C. is obtained.

IR(CHCl$_3$): 2940, 2838, 1725, 1695, 1564, 1460, 1432, 1323, 1267, 1108, 1015, 828 cm$^{-1}$.

C. Under the conditions of example 16K, 8.8 g of 3-(6-formyl-3-methoxy-2-pyridyl)-propionic acid methyl ester in 114 ml of 48% hydrobromic acid is reacted and worked up. 4.7 g of 3-(6-formyl-3-hydroxy-2-pyridyl)-propionic acid is obtained as crude product, which is dissolved in 350 ml of methanol for further reaction and is stirred in the presence of 14.4 g of Amberlyst 15 for 16 hours at room temperature. The methanol is removed in a vacuum, the residue is absorptively precipitated with concentrated ammonia solution, filtered on diatomaceous earth and the filter residue is washed with concentrated ammonia solution. The filtrate is neutralized with concentrated hydrochloric acid, adjusted to pH 5 with diluted hydrochloric acid, shaken out with ethyl acetate, the organic phase is dried on sodium sulfate and concentrated by evaporation. The crude product is chromatographed on silica gel with hexane/0–20% ethyl acetate. 2.5 g of 3-(6-formyl-3-hydroxy-2-pyridyl)-propionic acid methyl ester of melting point 92°–95° C. is obtained.

IR(CHCl$_3$): 3220 (broad), 2950, 2825, 1702, 1685, 1568, 1460, 1440, 1370, 1097, 1034, 928, 840 cm$^{-1}$.

D. Under the conditions of example 1 D, 510 mg of 3-(6-formyl-3-hydroxy-2-pyridyl)-propionic acid methyl ester is reacted with 730 mg of (1E)-6-bromo-1-(4-methoxyphenyl)-1-hexene, worked up, and the crude product is chromatographed on silica gel with hexane/0–10% ethyl acetate. 284 mg of 3-{6-formyl-3-[6-(4-methoxyphenyl)-(5E)-5-hexenyloxy]-2-pyridyl}-propionic acid methyl ester of melting point 66°–69° C. is obtained.

IR(CHCl$_3$): 2940, 2830, 1725, 1696, 1605, 1564, 1509, 1413, 1322, 1173, 1108, 1030, 967, 830 cm$^{-1}$.

E. 110 mg of sodium hydride dispersion (60%, Fluka company) is added to 2.4 ml of absolute dimethyl sulfoxide and stirred for 1 hour at 65° C. under argon atmosphere. 2.15 ml of this solution is added at room temperature to a solution of 668 mg of 3-carboxybenzyltriphenylphosphonium bromide in 1.75 ml of absolute dimethyl sulfoxide, and the mixture is stirred for 30 minutes at room temperature. Then, a solution of 280 mg of 3-{6-formyl-3-[6-(4-methoxyphenyl)-(5E)-5-hexenyloxy]-2-pyridyl}-propionic acid methyl ester in 1 ml of dimethyl sulfoxide is added, and the mixture is stirred under argon atmosphere for 16 hours at room temperature. For esterification, 0.13 ml of iodomethane is added and stirred for another 16 hours at room temperature. The reaction mixture is poured in ice water, shaken out with ethyl acetate, the organic phase is dried on sodium sulfate and concentrated by evaporation. 206 mg of 3-{6-[2-(3-methoxycarbonylphenyl)-(1E/Z)-1-ethenyl]-3-[6-(4-methoxyphenyl)-(5E)-5-hexenyloxy]-2-pyridyl}-propionic acid methyl ester is obtained as colorless oil, which is separated into the E- and Z-components by high-pressure liquid chromatography on reversed-phase silica gel (Nova-Pak HR C18) with methanol/water=9/1. 66 mg of 3-{6-[2-(3-methoxycarbonylphenyl)-(1E)-1-ethenyl]-3-[6-(4-methoxyphenyl)-(5E)-5-hexenyloxy]-2-pyridyl}-propionic acid methyl ester of melting point 81°–83° C. and 81 mg of 3-{6-[2-(3-methoxycarbonylphenyl)-(1Z)-1-ethenyl]-3-[6-(4-methoxyphenyl)-(5E)-5-hexenyloxy]-2-pyridyl}-propionic acid methyl ester are obtained as colorless oil.

(1E)-Compound:

IR(CHCl$_3$): 2925, 2855, 1720, 1608, 1575, 1510, 1455, 1290, 1175, 1030, 967 cm$^{-1}$.

(1Z)-Compound:

IR(Film): 2945, 2918, 2845, 1720, 1607, 1575, 1510, 1407, 1435, 1285, 1247, 1173, 1115, 1033, 966, 837, 757 cm$^{-1}$.

F. Under the conditions of example 3 C, 62 mg of 3-{6-[2-(3-methoxycarbonylphenyl)-(1E)-1-ethenyl]-3-[6-(4-methoxyphenyl)-(5E)-5-hexenyloxy]-2-pyridyl}-propionic acid methyl ester in 2.5 ml of methanol and 1 ml of tetrahydrofuran is saponified with 1.8 ml of 2n sodium hydroxide solution and worked up. The residue is stirred up with methanol and the crystallizate is suctioned off. 26 mg of the title compound is obtained as colorless crystals of melting point 193°–195° C.

IR(KBr): 3420 (broad), 2940, 1710, 1685, 1605, 1575, 1510, 1458, 1285, 1245, 1175, 1118, 1035, 963, 820, 756 cm$^{-1}$.

EXAMPLE 19

3-{6-[2-(3-Carboxyphenyl)-(1Z)-1-ethenyl]-3-[6-(4-methoxyphenyl)-(5E)-5-hexenyloxy]-2-pyridyl}-propionic acid Under the conditions of example 3 C, 82 mg of 3-{6-[2-(3-methoxycarbonyl-phenyl)-(1Z)-1-ethenyl]-3-[6-(4-methoxyphenyl)-(5E)-5-hexenyloxy]-2-pyridyl}-propionic acid methyl ester in 2.5 ml of methanol and 1 ml of tetrahydrofuran is saponified with 2 ml of 2n sodium hydroxide solution and worked up. 69 mg of the title compound is obtained as colorless oil.

IR(Film): 3500–2300, 1730, 1705, 1604, 1572, 1460, 1374, 1172, 1117, 1036, 965, 840 cm$^{-1}$.

EXAMPLE 20

3-{6-Carboxy-3-[6-(4-methoxyphenyl)-(5E)-5-hexenyloxy]-2-pyridyl}-propionic acid A. Under the conditions of example 1 B, a solution of 22 g of 2-iodo-3-methoxypyridine-6-carboxylic acid methyl ester in 50 ml of dimethylformamide is reacted with 12.6 g of acrylic acid methyl ester in the presence of 5.3 g of bis-triphenylphosphinepalladium(II) chloride, 25.9 g of potassium carbonate and 23.4 g of tetrabutylammonium bromide, worked up, and the crude product is chromatographed on silica gel with hexane/0–30% ethyl acetate. 11 g of 3-(3-methoxy-6-methoxycarbonyl-2-pyridyl)-(2E)-2-propenoic acid methyl ester of melting point 123°–126° C. is obtained.

IR(CHCl$_3$): 3005, 2960, 2850, 1725, 1715, 1648, 1577, 1470, 1434, 1333, 1282, 1174, 1142, 1110, 1023, 847 cm$^{-1}$.

B. Under the conditions of example 1 C, a solution of 11 g of 3-(3-methoxy-6-methoxycarbonyl-2-pyridyl)-(2E)-2-propenoic acid methyl ester in 600 ml of methanol is hydrogenated in the presence of 2.2 g of 10% palladium catalyst on activated carbon, worked up, and the crude product is chromatographed on silica gel with hexane/0–25% ethyl acetate. 8 g of 3-(3-methoxy-6-methoxycarbonyl-2-pyridyl)-propionic acid methyl ester of melting point 98°–100° C. is obtained.

IR(CHCl$_3$): 2960, 2855, 1730, 1720, 1575, 1468, 1434, 1336, 1140, 1116, 1023, 930, 845 cm$^{-1}$.

C. Under the conditions of example 16K, 6.5 g of 3-(3-methoxy-6-methoxycarbonyl-2-pyridyl)-propionic acid methyl ester in 60 ml of 48% hydrobromic acid is reacted and worked up. 4.1 g of 3-(6-carboxy-3-hydroxy-2-pyridyl)-propionic acid of melting point 210°–212° C. is obtained.

IR(KBr): 3420 (broad), 3330–2050, 1695, 1635, 1595, 1542, 1375, 1298, 1261, 1158, 1102, 980, 953, 880, 799 cm$^{-1}$.

D. 3.5 g of 3-(6-carboxy-3-hydroxy-2-pyridyl)-propionic acid is suspended in 25 ml of toluene, mixed with 32 ml of N,N-dimethylformamide-di-tert-butylacetal and heated for one hour to 75°–80° C. (bath temperature). The reaction mixture is washed with water, 10% sodium bicarbonate solution and saturated common salt solution, dried on sodium sulfate and concentrated by evaporation. The residue is chromatographed on silica gel with hexane/0–15% ethyl acetate. 1.65 g of 3-(6-tert-butoxycarbonyl-3-hydroxy-2-pyridyl)-propionic acid-tert-butyl ester of melting point 172°–174° C. is obtained.

IR(KBr): 2980, 2923, 1726, 1717, 1575, 1370, 1300, 1258, 1152, 1100, 1010, 848 cm$^{-1}$.

E. Under the conditions of example 1 D, 440 mg of 3-(6-tert-butoxycarbonyl-3-hydroxy-2-pyridyl)-propionic acid-tert-butyl ester is reacted with 367 mg of (1E)-6-bromo-1-(4-methoxyphenyl)-1-hexene, worked up, and the crude product is chromatographed on silica gel with hexane/0–8% ethyl acetate. 350 mg of 3-{6-tert-butoxycarbonyl-3-[6-(4-methoxyphenyl)-(5E)-5-hexenyloxy]-2-pyridyl}-propionic acid-tert-butyl ester is obtained as oil.

IR(CHCl$_3$): 2980, 2940, 1720, 1610, 1576, 1510, 1454, 1370, 1305, 1244, 1147, 1113, 1033, 970, 848 cm$^{-1}$.

F. A solution of 100 mg of 3-{6-tert-butoxycarbonyl-3-[6-(4-methoxyphenyl)-(5E)-5-hexenyloxy]-2-pyridyl}-propionic acid-tert-butyl ester in 5 ml of methanol is refluxed with 5 ml of 6n sodium hydroxide solution for 24 hours. The methanol is distilled off in a vacuum, the alkaline solution is acidified to pH 2 with 2n sulfuric acid and shaken out with dichloromethane. The organic phase is dried on sodium sulfate and concentrated by evaporation. 80 mg of the title compound of melting point 120°–123° C. is obtained.

IR(KBr): 3005, 2930, 1730, 1605, 1578, 1540, 1512, 1460, 1365, 1280, 1248, 1175, 1118, 1038, 963, 840, 798, 761 cm$^{-1}$.

EXAMPLE 21

3-{3-[6-(4-Methoxyphenyl)-(5E)-5-hexenyloxy]-6-[2-(4-carboxymethylphenyl)-ethinyl]-2-pyridyl}-propionic acid A. A solution of 100 g of 4-bromophenylacetic acid in 1.5 l of methanol is mixed with 232 g of Amberlyst 15, and the suspension is stirred for 48 hours at room temperature. The reaction mixture is suctioned off on diatomaceous earth, the filter residue is washed with dichloromethane, and the filtrate is concentrated by evaporation. The residue is taken up in ethyl acetate, washed with 10% sodium bicarbonate solution and saturated common salt solution, dried on sodium sulfate and concentrated by evaporation. 106 g of 4-bromophenylacetic acid methyl ester is obtained as oil.

IR(CHCl$_3$): 3000, 2852, 1722, 1593, 1486, 1435, 1340, 1255, 1160, 1070, 1010, 832 cm$^{-1}$.

B. A solution of 20 g of 4-bromophenylacetic acid methyl ester and 10.3 g of trimethylsilylacetylene in 650 ml of triethylamine is refluxed in the presence of 1.46 g of bis-triphenylphosphinepalladium(II) chloride and 227 mg of copper(I) iodide for 5 hours. The reaction mixture is concentrated by evaporation, the residue is spread between water and ethyl acetate, the organic phase is washed with saturated common salt solution, dried on sodium sulfate and concentrated by evaporation. The residue is chromatographed on silica gel with hexane/0–5% ethyl acetate. 17.1 g of 4-(2-trimethylsilylethinyl)-phenylacetic acid methyl ester is obtained as oily crude product.

C. A solution of 10 g of 4-(2-trimethylsilylethinyl)-phenylacetic acid methyl ester in 950 ml of tetrahydrofuran is mixed at 0° C. with 45 ml of a 1-molar solution of tetrabutylammonium fluoride in tetrahydrofuran. The reaction mixture is stirred for 15 minutes at 0° C. and for 2 hours at room temperature and then concentrated by evaporation. The residue is spread between water and ethyl acetate, the organic phase is dried on sodium sulfate, concentrated by evaporation and the residue is chromatographed on silica gel with hexane/0–7% ethyl acetate. 5.6 g of 4-ethinylphenylacetic acid methyl ester is obtained as oily crude product.

D. Under the conditions of example 5 A, 5 g of the crude 4-ethinylphenylacetic acid methyl ester is reacted with 7.9 g of 3-(3-hydroxy-6-iodo-2-pyridyl)-propionic acid methyl ester, worked up, and the crude product is chromatographed on silica gel with hexane/0–50% ethyl acetate. 3.6 g of 3-{3-hydroxy-6-[2-(4-methoxycarbonylmethylphenyl)-ethinyl]-2-pyridyl}-propionic acid methyl ester of melting point 122°–125° C. is obtained.

IR(CHCl$_3$): 2270 (broad), 2960, 2220, 1735, 1713, 1580, 1512, 1458, 1415, 1371, 1262, 1171, 1108, 1018, 840 cm$^{-1}$.

E. Under the conditions of example 1 D, 600 mg of 3-{3-hydroxy-6-[2-(4-methoxycarbonylmethylphenyl)-ethinyl]-2-pyridyl}-propionic acid methyl ester is reacted with 460 mg of (1E)-6-bromo-1-(4-methoxyphenyl)-1-hexene, worked up, and the crude product is chromatographed on silica gel with hexane/0–10% ethyl acetate. 504 mg of 3-{3-[6-(4-methoxyphenyl)-(5E)-5-hexenyloxy]-6-[2-(4-methoxycarbonylmethylphenyl)-ethinyl]-2-pyridyl}-propionic acid methyl ester is obtained as oil.

IR(CHCl$_3$): 3000, 2950, 2840, 2220, 1732, 1610, 1575, 1510, 1452, 1283, 1244, 1178, 1117, 1035, 970, 845, 827 cm$^{-1}$.

F. Under the conditions of example 3 C, 460 mg of 3-{3-[6-(4-methoxyphenyl)-(5E)-5-hexenyloxy]-6-[2-(4-methoxycarbonylmethylphenyl)-ethinyl]-2-pyridyl}-propionic acid methyl ester in 14 ml of methanol and 6 ml of tetrahydrofuran is saponified with 11.3 ml of 2n sodium hydroxide solution and worked up. 352 mg of the title compound is obtained as foam.

IR(KBr): 3420 (broad), 2930, 2830, 2210, 1732, 1708, 1605, 1575, 1510, 1450, 1245, 1178, 1110, 1032, 975, 822, 805 cm$^{-1}$.

EXAMPLE 22

3-{3-[6-(4-Methoxyphenyl)-(5E)-5-hexenyloxy-]-6-[carboxymethylphenyl)-ethyl]-2-pyridyl}-propionic acid A. Under the conditions of example 14 A, a solution of 500 mg of 3-{3-hydroxy-6-[2-(4-methoxycarbonylmethylphenyl)-ethinyl]- 2-pyridyl}-propionic acid-methyl ester in 5 ml of methanol is hydrogenated in the presence of 50 mg of 10% palladium catalyston activated carbon and worked up. The crude product is chromatographed on silica gel with hexane/ 0–30% ethyl acetate. 266 mg of 3-{3-hydroxy-6-[2-(4-methoxycarbonylmethylphenyl)-ethyl]-2-pyridyl}-propionic acid-methyl ester of melting point 90°–91° is obtained.

IR(CHCl$_3$): 3300 (broad), 2955, 1730, 1715, 1467, 1440, 1368, 1258, 1114, 1110, 1015 cm$^{-1}$.

B. Under the conditions of example 1 D, 235 mg of 3-{3-hydroxy-6-[2-(4-methoxycarbonylmethylphenyl)-ethyl]-2-pyridyl}-propionic acid methyl ester is reacted with 145 mg of (1E)-6-bromo-1-(4-methoxyphenyl)-1-hexene, worked up and the crude product is chromatographed on silica gel with hexane/0–10% ethyl acetate. 137 mg of 3-{3-[6-(4-methoxyphenyl)-(5E)-5-hexenyloxy]-6-[2-4-methoxycarbonylmethylphenyl)-ethyl]-2-pyridyl}-propionic acid methyl ester is obtained as oil.

IR(CHCl$_3$): 2940, 1730, 1608, 1580, 1508, 1458, 1173, 1117, 1030, 968 cm$^{-1}$.

C. Under the conditions of example 3 C, 100 mg of 3-{3-[6-(4-methoxyphenyl)-(5E)-5-hexenyloxy]-6-[2-(4-methoxycarbonylmethylphenyl)-ethyl]-2-pyridyl}-propionic acid methyl ester in 3 ml of methanol and 2.4 ml of 2n sodium hydroxide solution is saponified and worked up. 72 mg of the title compound is obtained as oil.

IR(CHCl$_3$): 2928, 2860, 1715, 1608, 1510, 1460, 1175, 1130, 967 cm$^{-1}$.

EXAMPLE 23

3-{3-[6-(4-Methoxyphenyl)-(5E)-5-hexenyloxy]-6-[2-(4-benzenesulfonamidocarbonyphenyl)-ethinyl]-2-pyridyl}-propionic acid A. 5 g of 4-iodobenzoic acid is added to a solution of 3.3 g of benzenesulfonamide, 2.68 g of 4-dimethylaminopyridine and 4.04 g of 1-(3-dimethylaminopropyl)-3-ethylcarbodiimide in 100 ml of dichloromethane, and the suspension is stirred for 18 hours at room temperature. The reaction mixture is diluted with 400 ml of dichloromethane, washed in succession with 400 ml portions of 10% hydrochloric acid, water and saturated common salt solution, the organic phase is dried on sodium sulfate and concentrated by evaporation. The residue is suspended in diethyl ether/ethyl acetate=1/1, and the crystallizate is suctioned off. 3.15 g of N-benzenesulfonyl-4-iodobenzoic acid amide of melting point 192°–193° C. is obtained.

IR(KBr): 3280, 1695, 1585, 1430, 1340, 1245, 1178, 1070, 1002, 895, 822, 758, 682, 580, 560 cm$^{-1}$.

B. Under the conditions of example 5A, 3.15 g of N-benzenesulfonyl-4-iodobenzoic acid is reacted with 1.3 g of trimethylsilylacetylene, worked up and the crude product is chromatographed on silica gel with dichloromethane/0–5% methanol. 3.1 g of N-benzenesulfonyl-4-(2-trimethylsilylethinyl)-benzoic acid amide is obtained as oil.

IR(Film): 2915, 2825, 1700, 1605, 1575, 1508, 1458, 1371, 1115, 1040, 965, 840 cm$^{-1}$.

C. Under the conditions of example 21 C, a solution of 3.1 g of N-benzenesulfonyl-4-(2-trimethylsilylethinyl)-benzoic acid amide in 200 ml of tetrahydrofuran is reacted with 9.5 ml of a 1-molar solution of tetrabutylammonium fluoride in tetrahydrofuran and worked up. 3 g of N-benzenesulfonyl-4-ethinylbenzoic acid amide is obtained as crude product.

D. Under the conditions of example 5 A, 1.31 g of the crude N-benzenesulfonyl-4-ethinylbenzoic acid amide is reacted with 1.9 g of 3-{6-iodo-3-[6-(4-methoxyphenyl)-(5E)-5-hexenyloxy]-2-pyridyl}-propionic acid methyl ester, worked up, and the crude product is chromatographed on silica gel with dichloromethane/0–5% methanol. 750 mg of 3-{3-[6-(4-methoxyphenyl)-(5E)-5-hexenyloxy]-6-[2-(4-benzenesulfonamidocarbonylphenyl)-ethinyl]-2-pyridyl}-propionic acid methyl ester is obtained as oil.

IR(CHCl$_3$): 2940, 2210, 1728, 1696, 1604, 1572, 1509, 1450, 1420, 1350, 1280, 1170, 1110, 1070, 966, 890, 825 cm$^{-1}$.

E. Under the conditions of example 3 C, 20 mg of 3-{3-[6-(4-methoxyphenyl)-(5E)-5-hexenyloxy]-6-[2-(4-benzenesulfonamidocarbonylphenyl)-ethinyl]-2-pyridyl}-propionic acid methyl ester is saponified in 0.7 methanol and 0.4 ml of 2n sodium hydroxide solution and worked up. 12 mg of the title compound is obtained as oil.

IR(KBr): 3430 (broad), 2930, 2860, 1708, 1608, 1578, 1515, 1455, 1250, 1177, 1118, 1075, 1020, 892, 762, 690, 582 cm$^{-1}$.

EXAMPLE 24

3-{6-[2-(4-Carboxyphenyl)-(1RS)-(2RS)-1,2-dihydroxyethyl]-3-decyloxy-2-pyridyl }-propionic acid A. A solution of 500 mg of 3-{6-[2-(4-methoxycarbonylphenyl)-ethinyl]-3-decyloxy-2-pyridyl}-propionic acid methyl ester in 4.6 ml of tetrachloromethane, 4.6 ml of acetonitrile and 7 ml of water is mixed with 303 mg of sodium periodate and stirred for 20 minutes at room temperature. Then, 2 mg of ruthenium(IV) oxide, hydrate is added, and the mixture is stirred for 48 hours at room temperature. The reaction mixture is added to water, shaken out with dichloromethane, the organic phase is dried on sodium sulfate and concentrated by evaporation. The crude product is chromatographed on silica gel with hexane/0–5% ethyl acetate. 249 mg of 3-{3-decyloxy-6-[2-(4-methoxycarbonylphenyl)-1,2-dioxoethyl-2-pyridyl}-propionic acid methyl ester is obtained as yellow oil.

IR(Film): 2930, 2860, 1730, 1695, 1565, 1455, 1440, 1410, 1363, 1344, 1280, 1215, 1108, 1020, 840 cm$^{-1}$.

B. A solution of 130 mg of 3-{3-decyloxy-6-[2-(4-methoxycarbonylphenyl)-1,2-dioxoethyl-2-pyridyl)-propionic acid methyl ester in 8 ml of methanol is mixed with 22 mg of sodium borohydride and stirred for 18 hours at room temperature. The reaction mixture is mixed with acetone, stirred for 30 minutes and concentrated by evaporation. The residue is spread between water and ethyl acetate, the organic phase is dried on sodium sulfate and concentrated by evaporation. 78 mg of 3-{3-decyloxy-6-[2-(4-methoxycarbonylphenyl)-(1RS)-(2RS)-1,2-dihydroxyethyl]-2-pyridyl}-propionic acid methyl ester of melting point 88°–92° C. is obtained.

IR(CHCl$_3$): 3400 (broad), 2925, 2855, 1720, 1614, 1582, 1460, 1438, 1282, 1115, 1018 cm$^{-1}$.

C. Under the conditions of example 3 C, 70 mg of 3-{3-decyloxy-6-[2-(4-methoxycarbonylphenyl)-(1RS)-(2RS)-1,2-dihydroxyethyl]-2-pyridyl}-propionic acid methyl ester in 2.5 ml of methanol and 1 ml of tetrahydrofuran is saponified with 1.9 ml of 2n sodium hydroxide solution and worked up. 49 mg of the title compound of melting point 162°–164° C. is obtained.

IR(KBr): 3420–3020, 2920, 2850, 1720, 1685, 1612, 1580, 1460, 1422, 1320, 1288, 1198, 1122, 1020, 935, 860 cm$^{-1}$.

EXAMPLE 25

3-{6-[2-(5-Carboxy-3-pyridyl)-ethinyl]-3-[6-(4-methoxyphenyl)-(5E)-5-hexenyloxy]-2-pyridyl}-propionic acid A. Under the conditions of example 21 B, 5 g of 5-bromonicotinic acid methyl ester is reacted with 2.43 g of trimethylsilylacetylene, worked up, and the crude product is chromatographed on silica gel with hexane/0–5% ethyl acetate. 734 mg of 5-(2-trimethlsilylethinyl)-nicotinic acid methyl ester is obtained as oil.

IR(KBr): 3045, 2955, 2160, 1724, 1585, 1560, 1445, 1430, 1298, 1250, 1216, 1160, 1110, 1020, 980, 912, 840 cm$^{-1}$.

B. Under the conditions of example 21 C, 464 mg of 5-(2-trimethylsilylethinyl)-nicotinic acid methyl ester is reacted with 2 ml of a 1-molar solution of tetrabutylammonium fluoride in tetrahydrofuran, worked up, and the residue is chromatographed on silica gel with hexane/0–7% ethyl acetate. 196 mg of 5-ethinylnicotinic acid methyl ester is obtained as oily crude product.

C. Under the conditions of example 5A, 184 mg of the crude 5-ethinylnicotinic acid methyl ester is reacted with 500 mg of 3-{6-iodo-3-[6-(4-methoxyphenyl)-(5E)-5-hexenyloxy]-2-pyridyl}-propionic acid methyl ester, worked up, and the crude product is chromatographed on silica gel with hexane/0–30% ethyl acetate and for complete purification subjected to high-pressure liquid chromatography on reversed-phase silica gel (Nova-Pak HR C18) with acetonitrile/water=75/25. 15 mg of 3-{6-[2-(5-methoxycarbonyl-3-pyridyl)-ethinyl]-3-[6-(4-methoxyphenyl)-(5E)-5-hexenyloxy]-2-pyridyl}-propionic acid methyl ester is obtained as oil.

IR(CHCl$_3$): 2957, 2930, 1728, 1605, 1573, 1510, 1455, 1292, 1112, 1030, 1015, 970 cm$^{-1}$.

D. Under the conditions of example 3 C, 15 mg of 3-{6-[2-(5-methoxycarbonyl-3-pyridyl)-ethinyl]-3-[6-(4-methoxyphenyl)-(5E)-5-hexenyloxy]-2-pyridyl}-propionic acid methyl ester in 0.5 ml of methanol and 0.5 ml of tetrahydrofuran is saponified with 2 ml of 2n sodium hydroxide solution and worked up. 10 mg of the title compound is obtained as an inner salt.

IR(KBr): 3440 (broad), 2930, 2855, 1575, 1580, 1458, 1262, 1110, 1030, 802 cm$^{-1}$.

EXAMPLE 26

3-{3-[6-(4-Methoxyphenyl)-(5E)-5-hexenyloxy]-6-[2-(3-trifluoromethanesulfonamidophenyl)-ethinyl]-2-pyridyl}-propionic acid A. 5.4 ml of trifluoromethanesulfonic anhydride is instilled in a solution of 5 g of 3-iodoaniline in 60 ml of chloroform and 3 g of triethylamine at 0°–5° C., and the mixture is then refluxed for 8 hours. The reaction mixture is poured in water, shaken out with dichloromethane, and the organic phase is concentrated by evaporation. The residue is taken up in 3n sodium hydroxide solution and shaken out with dichloromethane. The water phase is acidified to pH 2 with 10% sulfuric acid, shaken out with dichloromethane, the organic phase is dried on sodium sulfate and concentrated by evaporation. 6.3 g of N-(3-iodophenyl)-1,1,1-trifluoromethanesulfonamide of melting point 75°–77° C. is obtained.

IR(CHCl$_3$): 3360, 3280, 3120–3020, 2930, 2830, 1588, 1470, 1413, 1370, 1185, 1040, 1065, 1035, 925, 955, 825 cm$^{-1}$.

B. Under the conditions of example 5A, 6.2 g of N-(3-iodophenyl)-1,1,1-trifluoromethanesulfonamide is reacted with 2.07 g of trimethylsilylacetylene, worked up, and the crude product is chromatographed on silica gel with hexane/0–25% ethyl acetate. 2.72 g of N-[3-(2-trimethylsilylethinyl)-phenyl]-1,1,1-trifluoromethanesulfonamide is obtained as yellow oil.

IR(CHCl$_3$): 3365, 2962, 2160, 1608, 1583, 1482, 1417, 1375, 1250, 1190, 1140, 1005, 980, 850 cm$^{-1}$.

C. Under the conditions of example 21 C, 2 g of N-[3-(2-trimethylsilylethinyl)-phenyl]-1,1,1-trifluoromethanesulfonamide is reacted with 6.9 ml of a 1-molar solution of tetrabutylammonium fluoride in tetrahydrofuran and worked up. 387 mg of N-(3-ethinylphenyl)-1,1-trifluoromethanesulfonamide is obtained as oily crude product.

D. Under the conditions of example 5 A, 370 mg of crude N-(3-ethinylphenyl)-1,1,1-trifluoromethanesulfonamide is reacted with 735 mg of 3-{6-iodo-3-[6-(4-methoxyphenyl)-(5E)-5-hexenyloxy]-2-pyridyl}-propionic acid methyl ester, worked up, and the crude product is chromatographed on silica gel with hexane/0–20% ethyl acetate. 299 mg of 3-{3-[6-(4-methoxyphenyl)-(5E)-5-hexenyloxy]-6-[2-(3-trifluoromethanesulfonamidophenyl)-ethinyl]-2-pyridyl}-propionic acid methyl ester is obtained as oil.

IR(CHCl$_3$): 3360, 2930, 2850, 1730, 1605, 1580, 1510, 1451, 1420, 1373, 1195, 1142, 1114, 1035, 1005, 968 cm$^{-1}$.

E. Under the conditions of example 3 C, 100 mg of 3-{3-[6-(4-methoxyphenyl)-(5E)-5-hexenyloxy]-6-[2-(3-trifluoromethanesulfonamidophenyl)-ethinyl]-2-pyridyl}-propionic acid methyl ester in 3 ml of methanol is saponified with 2.3 ml of 2n sodium hydroxide solution and worked up. 86 mg of the title compound is obtained as oil.

IR(Film): 3700–2300, 2215, 1710, 1604, 1575, 1508, 1450, 1290, 1372, 1325, 1140, 1035, 967, 898, 829, 790 cm$^{-1}$.

EXAMPLE 27

5-{2-(2-Carboxyethyl)-3-[6-(4-methoxyphenyl)-(5E)-5-hexenyloxy]-6-pyridyl}-pentanoic acid A. Under the conditions of example 5A, 2 g of 3-(3-hydroxy-6-iodo-2-pyridyl)-propionic acid methyl ester is reacted with 0.8 g of 4-pentynoic acid methyl ester, worked up, and the crude product is chromatographed on silica gel with hexane/0–30% ethyl acetate. 1.6 g of 5-[3-hydroxy-2-(2-methoxycarbonylethyl)-6-pyridyl]-4-pentynoic acid methyl ester of melting point 119°–121° C. is obtained.

IR(CHCl$_3$): 3280 (broad), 2955, 2235, 1730, 1577, 1460, 1439, 1170, 1108, 1035, 985, 840 cm$^{-1}$.

B. Under the conditions of example 14 A, a solution of 1 g of 5-[3-hydroxy-2-(2-methoxycarbonylethyl)-6-pyridyl]-4-pentynoic acid methyl ester in 10 ml of methanol is hydrogenated in the presence of 100 mg of 10% palladium catalyst on activated carbon and worked up. The crude product is chromatographed on silica gel with hexane/0–50% ethyl acetate. 665 mg of 5-[3-hydroxy- 2-(2-methoxycarbonylethyl)-6-pyridyl]-pentanoic acid methyl ester of melting point 92°–95° C. is obtained.

IR(CHCl$_3$): 3320 (broad), 2950, 2860, 1725, 1600, 1465, 1439, 1410, 1368, 1170, 1108 cm$^{-1}$.

C. Under the conditions of example 1 D, 490 mg of 5-[3-hydroxy-2-(2-methoxycarbonylethyl)-6-pyridyl]-pentanoic acid methyl ester is reacted with 365 mg of (1E)-6-bromo-1-(4-methoxyphenyl)-1-hexene, worked up, and the crude product is chromatographed on silica gel with hexane/0–10% ethyl acetate. 293 mg of 5-{2-(2-methoxycarbonylethyl)-3-[6-(4-methoxyphenyl)-(5E)-5-hexenyloxy]-6-pyridyl}-pentanoic acid methyl ester is obtained as oil.

IR(CHCl$_3$): 2940, 2855, 1728, 1608, 1578, 1507, 1458, 1435, 1365, 1172, 1030, 965 cm$^{-1}$.

D. Under the conditions of example 3 C, 200 mg of 5-{2-(2-methoxycarbonyl-ethyl)-3-[6-(4-methoxyphenyl)-(5E)-5-hexenyloxy]-6-pyridyl}-pentanoic acid methyl ester in 6 ml of methanol and 1 ml of tetrahydrofuran is saponified with 5 ml of 2n sodium hydroxide solution and worked up. 170 mg of the title compound is obtained as colorless oil.

IR(CHCl$_3$): 2930, 2860, 2500 (broad), 1710, 1605, 1580, 1507, 1460, 1221, 1172, 1125, 1030, 965 cm$^{-1}$.

EXAMPLE 28

3-{6-(5-Hydroxy-1-pentynyl)-3-[6-(4-methoxyphenyl)-(5E)-5-hexenyloxy]-2-pyridyl}-propionic acid A. Under the conditions of example 5 A, 5 g of 3-(3-hydroxy-6-iodo-2-pyridyl)-propionic acid methyl ester is reacted with 1.37 g of 4-pentyn-1-ol, worked up, and the crude product is chromatographed on silica gel with hexane/0–4% methanol. 1.2 g of 3-[3-hydroxy-6-(5-hydroxy-1-pentynyl)-2-pyridyl]-propionic acid methyl ester is obtained as colorless oil.

IR(CHCl$_3$): 3270, 2950, 2230, 1708, 1572, 1455, 1410, 1362, 1168, 1103, 938, 835 cm$^{-1}$.

B. Under the conditions of example 1 D, 400 mg of 3-[3-hydroxy-6-(5-hydroxy-1-pentynyl)-2-pyridyl]-(propionic acid methyl ester is reacted with 410 mg of (1E)-6-bromo-1-(4-methoxyphenyl)-1-hexene, worked up, and the crude product is chromatographed on silica gel with hexane/0–27.5% ethyl acetate. 293 mg of 3-{6-(5-hydroxy-1-pentynyl)-3-[6-(4-methoxyphenyl)-(5E)-5-hexenyloxy]-2-pyridyl}-propionic acid methyl ester is obtained as colorless oil.

IR(CHCl$_3$): 3440 (broad), 2940, 2230, 1727, 1606, 1572, 1507, 1448, 1295, 1172, 115, 1030, 965, 823 cm$^{-1}$.

C. Under the conditions of example 3 C, 152 mg of 3-{6-(5-hydroxy-1-pentynyl)-3-[6-(4-methoxyphenyl)-(5E)-5-hexenyloxy]- 2-pyridyl}-propionic acid methyl ester is saponified to 4.5 ml of 2n sodium hydroxide solution and worked up. 147 mg of the title compound of melting point 115°–117° C. is obtained.

IR(CHCl$_3$): 3400 (broad), 2935, 2540 (broad), 2235, 1720, 1608, 1577, 1510, 1453, 1275, 1175, 1034, 968, 830 cm$^{-1}$.

EXAMPLE 29

3-{6-(5-Hydroxypentyl)-3-[6-(4-methoxyphenyl)-(5E)-5-hexenyloxy]-2pyridyl}-propionic acid A. Under the conditions of example 14 A, a solution of 700 mg of 3-[3-hydroxy-6-(5-hydroxy-1-pentynyl)-2-pyridyl]-propionic acid methyl ester in 25 ml of methanol is hydrogenated in the presence of 100 mg of 10% palladium catalyst on activated carbon and worked up. The crude product is chromatographed on silica gel with hexane/10–30% ethyl acetate. 537 mg of 3-hydroxy-6-(5-hydroxypentyl)-2-pyridyl]-propionic acid methyl ester is obtained as oil, which, under the conditions of example 1 D, is further reacted with 584 mg of (1E)-6-bromo-1-(4-methoxyphenyl)-1-hexene and is worked up. After chromatography of the crude product on silica gel with hexane/0–25% ethyl acetate, 405 mg of 3-{6-(5-hydroxypenyl)-3-[6-(4-methoxyphenyl)-(5E)-5-hexenyloxy]-2-pyridyl}-propionic acid is obtained as oil.

IR(Film): 3400 (broad), 2930, 2850, 1737, 1670, 1608, 1508, 1458, 1245 cm$^{-1}$.

B. Under the conditions of example 3 C, 400 mg of 3-{6-(5-hydroxypentyl)-3-[6-(4-methoxyphenyl)-(5E)-5-hexenyloxy]-2-pyridyl}-propionic acid methyl ester in 20 ml of methanol is saponified with 12 ml of 2n sodium hydroxide solution and worked up. 322 mg of the title compound is obtained as oil.

IR(Film): 3300 (broad), 2930, 2850, 1720, 1604, 1508, 1455, 1242 cm$^{-1}$.

EXAMPLE 30

3-{6-[2-(4-Carboxyphenyl)-ethinyl-3-[6-(4-methoxyphenyl)-(5E)-5-hexenyloxy]-2-pyridyl}-propionic acid, dilithium salt A solution of 500 mg of 3-{6-[2-(4-methoxycarbonylphenyl)-ethinyl-3-[6-(4-methoxyphenyl)-(5E)-5-hexenyloxy]-2-pyridyl}-propionic acid ester in 12 ml each of methanol, tetrahydrofuran and water is mixed with 113 mg of lithium hydroxide and stirred for 16 hours at room temperature. The solvent is distilled off in a vacuum, and the residue is chromatographed on reversed-phase silica gel (RP-18 material) with water/10–30% methanol. The desired fractions are combined, the methanol is distilled off in a vacuum, and the remaining aqueous solution is freeze-dried. 471 mg of the title compound is obtained as colorless, amorphous solid.

IR(KBr): 3420 (broad), 2930, 2210, 1602, 1448, 1405, 1245, 1245, 1113 cm$^{-1}$.

EXAMPLE 31

3-{6-[2-(3-Carboxyphenyl)-ethyl-3-[6-(4-methoxyphenyl)-(5E)-5-hexenyloxy]-2-pridyl}-propionic acid, dilithium salt A. Under the conditions of example 5A, 9.2 g of 3-(3-hydroxy-6-iodo-2-pyridyl)-propionic acid methyl ester is reacted with 4.8 g of 3-ethinylbenzoic acid methyl ester, worked up, and the crude product is chromatographed on silica gel with hexane/0–20% ethyl acetate. 4.7 g of 3-{3-hydroxy-6-[2-(3-methoxycarbonylphenyl)-ethinyl]-2-pyridyl}-propionic acid methyl ester of melting point 125°–127° C. is obtained.

IR(CHCl$_3$): 3250 (broad), 2950, 1718, 1453, 1435, 1258, 1098, 1010 cm$^{-1}$.

B. Under the conditions of example 14 A, a solution of 1.25 g of 3-{3-hydroxy-6-[2-(3-methoxycarbonylphenyl)-ethinyl]-2-pyridyl}-propionic acid ester in 50 ml of methanol and 10 ml of ethanol is hydrogenated in the presence of 125 mg of 10% palladium catalyst on activated carbon and worked up. 1.24 g of 3-{3-hydroxy-6-[2-(3-methxoycarobnylphenyl)-ethinyl]-2-pyridyl}-propionic acid methyl ester of melting point 130°–132° C. is obtained.

IR(CHCl$_3$): 3300 (broad), 2950, 1710, 1465, 1440, 1368, 1285, 1108 cm$^{-1}$.

C. Under the conditions of example 1 D, 1.24 g of 3-{3-hydroxy-6-[2-(3-methoxycarbonylphenyl)-ethinyl]-2-pyridyl}-propionic acid methyl ester is reacted with 970 mg of (1E)-6-bromo-1-(4-methoxyphenyl)-1-hexene, worked up, and the crude product is chromatographed on silica gel with hexane/0–7.5% ethyl acetate. 1.1 g of 3-{6-[2-(3-methoxycarbonylphenyl)-ethyl]-3-[6-(4-methoxyphenyl)-(5E)-5-hexenyloxy]-2-pyridyl}-propionic acid methyl ester is obtained as colorless oil.

IR(CHCl$_3$): 2935, 1720, 1604, 1580, 1504, 1455, 1112, 1027 cm$^{-1}$.

D. Under the conditions of example 30, a solution of 500 mg of 3-{6-[2-(3-methoxycarbonylphenyl)-ethyl]-3-[6-(4-methoxyphenyl)-(5E)-5-hexenyloxy]-2-pyridyl}-propionic acid methyl ester in 12 ml each of methanol, tetrahydrofuran and water is saponified with 115 mg of lithium hydroxide, worked up and chromatographed. 480 mg of the title compound is obtained as colorless, amorphous solid.

IR(KBr): 3370 (broad), 2940, 1580, 1423, 1261, 1240, 1172, 1113, 960 cm$^{-1}$.

EXAMPLE 32

3-{6-[2-(4-Carboxyphenyl)-ethyl-3-[6-(4-methoxyphenyl)-(5E)-5-hexenyloxy]-2-pyridyl}-propionic acid, bis-tris-(hydroxymethyl)-aminomethane salt Under the conditions of example 8, 100 mg of 3-{6-[2-(4-carboxyphenyl)-ethyl-3-[6-(4-methoxyphenyl)-(5E)-5-hexenyloxy]-2-pyridyl}-propionic acid is reacted with tris-(hydroxymethyl)-aminomethane and worked up. 79 mg of the title compound of melting point 95°–100° C. is obtained.

IR(KBr): 3400–2500, 1610, 1585, 1520, 1460, 1395, 1240, 1177, 1065, 1030 cm$^{-1}$.

EXAMPLE 33

3-{6[2-(3-Carboxyphenyl)-ethinyl-3-[6-(4-methoxyphenyl)-(5E)-5-hexenyloxy]-2-pyridyl}-propionic acid, disodium salt A solution of 300 mg of 3-{6-[2-(3-carboxyphenyl)-ethinyl-3-[6-(4-methoxyphenyl)-(5E)-5-hexenyloxy]-2-pyridyl}-propionic acid in 5 ml of tetrahydrofuran is neutralized to 6 ml of 0.1n sodium hydroxide solution, the tetrahydrofuran is distilled off in a vacuum, and the remaining aqueous solution is freeze-dried. 258 mg of the title compound is obtained as light yellow amorphous solid.

IR(KBr): 3420 (broad), 2930, 2210, 1608, 1565, 1509, 1450, 1425, 1393, 1245, 1112, 1033 cm$^{-1}$.

We claim:
1. A pyridine compound of general formula I

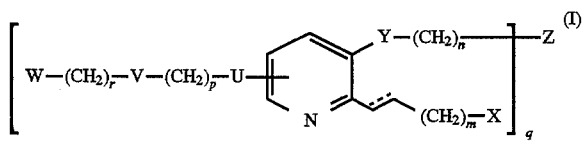

wherein
......  is a single bond or a double bond,
m, n, p and r is a number from 0 to 5,
q is 1 or 2,
U is the grouping —CH$_2$—CH$_2$—, —CH=CH—, or —C≡C—,
V is a phenyl radical or a pyridyl radical,
W is a hydrogen atom, a halogen atom, an alkyl group with up to 4 carbon atoms, a trifluoromethyl group, an alkylsulfonylamino group, a trifluoromethylsulfonylamino group, an arylsulfonylaminocarbonyl group, a free, esterified or amidated carboxyl group, or a hydroxy group,
X is a free, esterified or amidated carboxyl group,
Y is an oxygen atom or a methylene group, and if q is 2, then Z is a single bond; otherwise
Z is an alkyl group or alkylene group with at most 8 carbon atoms or a phenyl radical, phenoxy radical or styryl radical optionally substituted by alkyl groups with at most 4 carbon atoms, alkoxy groups with at most 4 carbon atoms, 1-oxoalkyl groups with at most 4 carbon atoms, halogen atoms and/or trifluoromethyl groups, and their salts with physiologically compatible bases.

2. 3-{6-[2-(3-Carboxyphenyl)-ethinyl]-3-[6-(4-methoxyphenyl)-(5E)-5-hexenyloxy]-2-pyridyl}-propionic acid a compound of claim 1.

3. 3-{6-[2-(4-Carboxyphenyl)-ethinyl]-3-[6-(4-methoxyphenyl)-(5E)-5-hexenyloxy]-2-pyridyl}-propionic acid a compound of claim 1.

4. 3-{6-[2-(4-Carboxyphenyl)-ethinyl]-3-[6-(4-methoxyphenyl)-(5E)-5-hexenyloxy]-2-pyridyl}-propionic acid, bis-tris-(hydroxymethyl)-aminomethane salt a compound of claim 1.

5. 3-{6-[2-(4-Carboxyphenyl)-ethinyl]-3-decyloxy-2-pyridyl}-propionic acid a compound of claim 1.

6. 3-{6-[2-(4-Carboxyphenyl)-ethinyl]-3-[3-(4-acetyl-3-methoxy-2-(propyl)phenoxy)-propoxy]-2pyridyl}-propionic acid a compound of claim 1.

7. 3-{6-[2-(4-Carboxyphenyl)-ethinyl]-3-[(3RS)-3,7-dimethyl-6-octenyloxy]-2-pyridyl}-propionic acid a compond of claim 1.

8. 3-{3-[6-(4-methoxyphenyl)-(5E)-5-hexenyloxy]-6-(2-phenylethinyl)-2-pyridyl}-propionic acid a compond of claim 1.

9. 3-{6-[2-(3-Carboxyphenyl)-ethinyl]-3-[6-(4-methoxyphenyl)-(5E)-5-hexenyl-oxy]-2-pyridyl}-propionic acid, bis-tris-(hydroxymethyl)-aminomethane salt a compond of claim 1.

10. 3-{6-[2-(4-Carboxyphenyl)-ethyl]-3-[6-(4-methoxyphenyl)-(5E)-5-hexenyl-oxy]-2-pyridyl}-propionic acid a compond of claim 1.

11. 1,10-Bis-{2-(2-carboxyethyl)-6-[2-(4-carboxyphenyl)-ethinyl]-3-pyridyloxy}-decane a compond of claim 1.

12. 3-{6-[2-(3-Carboxyphenyl)-(1E)-1-ethenyl]-3-[6-(4-methoxyphenyl)-(5E)-5-hexenyloxy]-2-pyridyl}-propionic acid a compond of claim 1.

13. 3-{6-[2-(3-Carboxyphenyl)-(1Z)-1-ethenyl]-3-[6-(4-methoxyphenyl)-(5E)-5-hexenyloxy]-2-pyridyl}-propionic acid a compond of claim 1.

14. 3-{3-[6-(4-Methoxyphenyl)-(5E)-5-hexenyloxy]-6-[2-(4-carboxymethylphenyl)-ethinyl]-2-pyridyl}-propionic acid a compond of claim 1.

15. 3-{3-[6-(4-Methoxyphenyl)-(5E)-5-hexenyloxy]-6-[2-(4-carboxymethylphenyl)-ethyl]-2-pyridyl}-propionic acid a compond of claim 1.

16. 3-{3-[6-(4-Methoxyphenyl)-(5E) -5-hexenyloxy]-6-[2-(4-benzenesulfonamidocarbonylphenyl)-ethinyl]-2-pyridyl }-propionic acid a compond of claim 1.

17. 3-{6-[2-(5-Carboxy-3-pyridyl)-ethinyl]-3-[6-(4-methoxyphenyl)-(5E)-5-hexenyloxy]-2-pyridyl}-propionic acid a compond of claim 1.

18. 3-{3-[6-(4-Methoxyphenyl)-(5E)-5-hexenyloxy]-6-[2-(3-trifluoromethanesulfonamidophenyl)-ethinyl]-2-pyridyl}-propionic acid a compond of claim 1.

19. A pharmaceutical composition comprising, an effective amount of a pyridine compound of claim 1.

20. A pharmaceutical composition of claim 19, wherein said compound is a leukotriene-B$_4$-antagonist.

* * * * *